United States Patent
Hematti et al.

(10) Patent No.: US 11,738,046 B2
(45) Date of Patent: Aug. 29, 2023

(54) MACROPHAGE CELL THERAPY TO TREAT ORTHOPEDIC INJURY

(71) Applicant: Wisconsin Alumni Research Foundation, Madison, WI (US)

(72) Inventors: Peiman Hematti, Middleton, WI (US); Connie Chamberlain, Monona, WI (US); Anna Elizabeth Breiner Clements, Madison, WI (US); Ray Vanderby, Madison, WI (US); John A. Kink, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 733 days.

(21) Appl. No.: 16/179,298

(22) Filed: Nov. 2, 2018

(65) Prior Publication Data
US 2019/0134090 A1 May 9, 2019

Related U.S. Application Data

(60) Provisional application No. 62/581,128, filed on Nov. 3, 2017.

(51) Int. Cl.
| | |
|---|---|
| A61K 35/15 | (2015.01) |
| C12N 5/0786 | (2010.01) |
| C12N 5/0775 | (2010.01) |
| A61K 9/00 | (2006.01) |
| A61P 29/00 | (2006.01) |
| A61P 21/00 | (2006.01) |

(52) U.S. Cl.
CPC ............ *A61K 35/15* (2013.01); *A61K 9/0019* (2013.01); *C12N 5/0645* (2013.01); *C12N 5/0663* (2013.01); *A61P 21/00* (2018.01); *A61P 29/00* (2018.01); *C12N 2502/1358* (2013.01)

(58) Field of Classification Search
CPC ....... A61K 35/15; A61K 9/0019; A61P 21/00; A61P 29/00; C12N 5/0645; C12N 5/0663; C12N 2502/1358
USPC ............................... 424/93.71; 435/372, 390
See application file for complete search history.

(56) References Cited

U.S. PATENT DOCUMENTS

| | | | |
|---|---|---|---|
| 8,647,678 B2 | 2/2014 | Hematti | |
| 2015/0147300 A1* | 5/2015 | Woodell-May | C12N 5/0667 435/375 |
| 2016/0082042 A1* | 3/2016 | Hematti | A61K 45/06 424/93.71 |
| 2018/0282698 A1 | 10/2018 | Hematti | |

OTHER PUBLICATIONS

Schlundt et al., "Macrophages in bone fracture healing: Their essential role in endochondral ossification" epub Oct. 31, 2015, Bone 106, p. 78-89.*

Chamberlain et al., "The Influence of Macrophage Depletion on Ligament Healing", 2011, Connective Tissue Research 52(3), p. 203-211.*

Menendez et al., "Sequential analysis of CD34+ and CD34+ cell subsets in peripheral blood and leukapheresis products from breast cancer patients mobilized with SCF plus G-CSF and cyclophosphamide", 2001, Leukemia 15, p. 430-439.*

Kastelowitz et al. (2014) ChemBioChem, vol. 15, 923-928.*

Frantz et al. (2010) J. Cell. Sci., vol. 123, 4195-4200.*

Abtahi, AM, et al. "Factors affecting healing after arthroscopic rotator cuff repair." World journal of orthopedics 6.2 (2015): 211.

Battiwalla M, et al. Mesenchymal stem cells in hematopoietic stem cell transplantation. Cytotherapy 2009;11:503-515.

Benoit M, et al (2008) Macrophage polarization in bacterial infections. J Immunol 181: 3733-3739.

Bruesch, M., et al. "Epidemiology, treatment and follow-up of acute ligamentous knee injuries in Alpine skiing." Zeitschrift fur Unfallchirurgie und Versicherungsmedizin: offizielles Organ der Schweizerischen Gesellschaft fur Unfallmedizin und Berufskrankheiten= Revue de traumatologie et d'assicurologie: organe officiel de la Societe suisse de . . . (1993): 144-155.

Cantu DA, et al. Cell encapsulating biomaterial regulates mesenchymal stromal/stem cell differentiation and macrophage immunophenotype. Stem Cells Transl Med 2012;1:740-749.

Chamberlain CS et al., The Influence of Exosome-Educated Macrophages on Tendon Healing, Presentation, Orthopaedic Research Society, Mar. 2018.

Chamberlain CS, et al (2011) Quantification of collagen organization and extracellular matrix factors within the healing ligament. Microsc Microanal 17: 779-787.

Chamberlain CS, et al. "Temporal healing in rat achilles tendon: ultrasound correlations." Annals of biomedical engineering 41.3 (2013): 477-487.

Chamberlain CS, et al. Effects of bmp-12-releasing sutures on achilles tendon healing. Tissue Engineering Part A 2015;21:916-927.

Chamberlain CS, et al. Gene profiling of the rat medial collateral ligament during early healing using microarray analysis. Journal of applied physiology. 2011;111(2):552-65. Epub May 21, 2011.

Chamberlain CS, et al. Interleukin Expression after Injury and the Effects of Interleukin-1 Receptor Antagonist. PloS one. 2013;8(8).

Chamberlain CS, et al. The influence of interleukin-4 on ligament healing. Wound repair and regeneration : official publication of the Wound Healing Society [and] the European Tissue Repair Society. 2011;19(3):426-35. Epub Apr. 27, 2011.

Chamberlain CS, et al. The influence of macrophage depletion on ligament healing. Connective tissue research. 2011;52(3):203-11. Epub Dec. 2, 2010.

Chamberlain CS, et al. The spatio-temporal dynamics of ligament healing. Wound repairand regeneration : official publication of the Wound Healing Society [and] the European Tissue Repair Society. 2009;17(2):206-15. Epub Mar. 27, 2009.

(Continued)

*Primary Examiner* — Anne Marie S Wehbe
(74) *Attorney, Agent, or Firm* — McDonnell Boehnen Hulbert & Berghoff LLP

(57) ABSTRACT

An ex vivo generated population of tissue-specific alternatively-activated macrophages and methods of making and using such macrophages for treating orthopedic injury are provided.

10 Claims, 10 Drawing Sheets
(10 of 10 Drawing Sheet(s) Filed in Color)

(56) References Cited

OTHER PUBLICATIONS

Chamberlain CS, et al.. Interleukin-1 receptor antagonist modulates inflammation and scarring after ligament injury. Connective tissue research. 2014;55(3):177-86.
Chiodo CP, et al (2006) Current concepts review: acute ruptures of the achilles tendon. Foot & Ankle International 27:305-313.
Consiglio M, et al. Human-in the-Loop Experimental Research for Detect and Avoid. Ieeeaaia Digit Avion. 2015.
Da Silva CL, et al. A human stromal-based serum-free culture system supports the ex vivo expansion/maintenance of bone marrow and cord blood hematopoietic stem/progenitor cells. Exp Hematol 2005;33:828-835.
Dachir S, et al. Beneficial effects of activated macrophages on sulfur mustard induced cutaneous burns, an in vivo experience. Cutan Ocul Toxicol 2014;33:317-326.
Danon D, et al. Treatment of human ulcers by application of macrophages prepared from a blood unit. Exp Gerontol 1997;32:633-641.
Dayan V, et al. Mesenchymal stromal cells mediate a switch to alternatively activated monocytes/macrophages after acute myocardial infarction. Basic Res Cardiol 2011;106:1299-1310.
De Jong JP, et al. (2014) The incidence of acute traumatic tendon injuries in the hand and wrist: a 10-year population-based study. Clin Orthop Surg 6: 196-202.
Delavary BM, et al. Macrophages in skin injury and repair. Immunobiology. 2011;216(7)753-62. Epub Feb. 2, 2011.
Deng W, et al. (2015) Mesenchymal stem cells promote CD206 expression and phagocytic activity of macrophages through IL-6 in systemic lupus erythematosus. Clin Immunol 161: 209-216.
Dominici, M., et al. "Minimal criteria for defining multipotent mesenchymal stromal cells. The International Society for Cellular Therapy position statement." Cytotherapy 8.4 (2006): 315-317.
Falanga V, et al. Full-thickness wounding of the mouse tail as a model for delayed wound healing: Accelerated wound closure in smad3 knock-out mice. Wound Repair Regen 2004;12:320-326.
Favaro E, et al. Human mesenchymal stem cell-derived 474 microvesicles modulate t cell response to islet antigen glutamic acid decarboxylase in patients with type 1 diabetes. Diabetologia 2014;57:1664-1673.
Frisch KE, et al. The influence of partial and full thickness tears on infraspinatus tendon strain patterns. J Biomech Eng 2014;136:051004.
Frisch KE, et al. (2012) Quantification of collagen organization using fractal dimensions and Fourier transforms. Acta Histochemica 114(2):140-144.
Gasse P, et al. IL 1R1/MyD88 signaling and the inflammasome are essential in pulmonary inflammation and fibrosis in mice. The Journal of clinical investigation. 2007;117(12):3786-99. Epub Nov. 10, 2007.
Godwin JW, et al. (2013) Macrophages are required for adult salamander limb regeneration. Proc Natl Acad Sci U S A 110: 9415-9420.
Goren I, et al. A transgenic mouse model of inducible macrophage depletion: Effects of diphtheria toxin-driven lysozyme m-specific cell lineage ablation on wound inflammatory, angiogenic, and contractive processes. Am J Pathol 2009;175:132-147.
Hanson SE, et al. The effect of mesenchymal stromal cell-hyaluronic acid hydrogel constructs on immunophenotype of macrophages. Tissue Eng Part A 2011;17:2463-2471.
Huber R, et al. Regulation of C/EBP beta and resulting functions in cells of the monocytic lineage. Cell Signal. 2012;24(6):1287-96.
Hurschler, et al. "Scanning electron microscopic characterization of healing and normal rat ligament microstructure under slack and loaded conditions." Connective tissue research 44.2 (2003): 59-68.
Jain NB, et al. Epidemiology of musculoskeletal upper extremity ambulatory surgery in the united states. BMC Musculoskelet Disord 2014;15:4.

Jensen KT, et al. Early inflammatory response of knee ligaments to prolotherapy in a rat model. Journal of orthopaedic research : official publication of the Orthopaedic Research Society. 2008;26(6):816-23. Epub Feb. 2, 2008.
Jetten et al., 2014 "Wound administration of M2-polarized macrophages does not improve murine cutaneous healing responses" PLoS ONE 9(7).
Kavanagh DM, et al. A molecular toggle after exocytosis sequesters the presynaptic syntaxin1a molecules involved in prior vesicle fusion. Nat Commun. 2014;5.
Kim J, et al. (2009) Mesenchymal stem cell-educated macrophages: a novel type of alternatively activated macrophages. Exp Hematol 37: 1445-1453.
King SN, et al. In vitro characterization of macrophage interaction with mesenchymal stromal cell-hyaluronan hydrogel constructs. J Biomed Mater Res A 2014;102:890-902.
Kourembanas S. Exosomes: Vehicles of intercellular signaling, biomarkers, and vectors of cell therapy. Annu Rev Physiol 2015;77:13-27.
Li Q, et al. IL-17 and IFN-gamma production in peripheral blood following BCG vaccination and *Mycobacterium tuberculosis* infection in human. European review for medical and pharmacological sciences. 2012;16(14):2029-36. Epub Dec. 18, 2012.
Ling Y, et al. [Detection of KRAS, BRAF, PIK3CA and EGFR gene mutations in colorectal carcinoma]. Zhonghua bing li xue za zhi Chinese journal of pathology. 2012;41(9):590-4. Epub Nov. 20, 2012.
Ling Y, et al. Analysis of genetic diversity among wild bermudagrass germplasm from southwest China using SSR markers. Genetics and molecular research : GMR. 2012;11(4):4598-608. Epub Oct. 26, 2012.
Lu H, et al. Temporal and spatial expression of podocyte-associated molecules are accompanied by proteinuria in IgA nephropathy rat model. Physiological research / Academia Scientiarum Bohemoslovaca. 2013;62(1):35-45. Epub Nov. 24, 2012.
Lucas T, et al. Differential roles of macrophages in diverse phases of skin repair. J Immunol 2010;184:3964-3977.
Mantovani A, et al. Macrophage plasticity and polarization in tissue repair and remodelling. J Pathol 2013;229:176-185.
Mantovani et al., "The chemokine system in diverse forms of macrophage activation and polarization." Trends in immunology 25.12 (2004): 677-686.
Martinez FO, et al. Alternative activation of macrophages: An immunologic functional perspective. Annu Rev Immunol 2009;27:451-483.
Martinez FO, et al. Macrophage activation and polarization. Front Biosci 2008;13:453-461.
Mirza R, et al. Selective and specific macrophage ablation is detrimental to wound healing in mice. Am J Pathol 2009;175:2454-2462.
Misra, Arpit. "Common sports injuries: incidence and average charges." ASPE [homepage on the Internet] (2014).
Zuloff-Shani A, et al. Macrophage suspensions prepared from a blood unit for treatment of refractory human ulcers. Transfus Apher Sci 2004;30:163-167.
Moestrup SK, et al.(2004) CD163: a regulated hemoglobin scavenger receptor with a role in the anti-inflammatory response. Ann Med 36: 347-354.
Mosser, David M. "The many faces of macrophage activation." Journal of leukocyte biology 73.2 (2003): 209-212.
Mosser, et al. "Exploring the full spectrum of macrophage activation." Nature reviews immunology 8.12 (2008): 958.
Nemeth K, et al. Bone marrow stromal cells attenuate sepsis via prostaglandin e(2)-dependent reprogramming of host macrophages to increase their interleukin-10 production. Nat Med 2009;15:42-49.
Neuman BW, et al. Atlas of coronavirus replicase structure. Virus research. 2014;194:49-66.
Oliva, F., et al. "Thyroid hormones enhance growth and counteract apoptosis in human tenocytes isolated from rotator cuff tendons." Cell death & disease 5.7 (2014): e1329.
Oliva, Francesco, et al. "Epidemiology of the rotator cuff tears: a new incidence related to thyroid disease." Muscles, ligaments and tendons journal 4.3 (2014): 309.

(56) References Cited

OTHER PUBLICATIONS

Pollard, Jeffrey W. "Trophic macrophages in development and disease." Nature reviews immunology 9.4 (2009): 259.
Provenzano PP, et al. Intrinsic fibroblast-mediated remodeling of damaged collagenous matrices in vivo. Matrix biology : journal of the International Society for Matrix Biology 2005;23(8):543-55. Epub Feb. 8, 2005.
Ramji DP, et al. CCAAT/enhancer-binding proteins: structure, function and regulation. The Biochemical journal. 2002;365(Pt 3):561-75. Epub May 15, 2002.
Raposo, Graca, et al. "B lymphocytes secrete antigen-presenting vesicles." Journal of Experimental Medicine 183.3 (1996): 1161-1172.
Sica A, et al. Macrophage plasticity and polarization: In vivo veritas. 450 J Clin Invest 2012;122:787-795.
Sindrilaru A, et al. (2011) An unrestrained proinflammatory M1 macrophage population induced by iron impairs wound healing in humans and mice. J Clin Invest 121: 985-997.
Stoorvogel, Willem, et al. "The biogenesis and functions of exosomes." Tiaffic 3.5 (2002): 321-330.
Stout, Robert D., et al. "Macrophages sequentially change their functional phenotype in response to changes in microenvironmental influences." The Journal of Immunology175.1 (2005): 342-349.
Thery C, et al. Isolation and characterization of exosomes from cell culture supernatants and biological fluids. Curr Protoc Cell Biol 2006;Chapter 3:Unit 3 22.
Trivedi P, et al. Derivation and immunological characterization of mesenchymal stromal cells from human embryonic stem cells. Exp Hematol 2008;36:350-359.
Voleti, P.B., et al. "Tendon healing: repair and regeneration." Annual review of biomedical engineering 14 (2012): 47-71.
Woo, et al. "Biomechanics of knee ligaments: injury, healing, and repair." Journal of biomechanics 39.1 (2006): 1-20.
Woolf, Anthony D., and Bruce Pfleger. "Burden of major musculoskeletal conditions." Bulletin of the World Health Organization 81 (2003): 646-656.
Wynn TA (2004) Fibrotic disease and the T(H)1/T(H)2 paradigm. Nature Reviews Immunology 4: 583-594.
Xiao W, et al. (2008) Regulation of myeloproliferation and M2 macrophage programming in mice by Lyn/Hck, SHIP, and Stat5. J Clin Invest 118: 924-934.
Yin F, et al. Bone marrow mesenchymal stromal cells to treat tissue damage in allogeneic stem cell transplant recipients: Correlation of biological markers with clinical responses. Stem Cells 2014;32:1278-1288.
Peat, G., et al. "Population-wide incidence estimates for soft tissue knee injuries presenting to healthcare in southern Sweden: data from the Skåne Healthcare Register." Arthritis research & therapy 16.4 (2014): R162.
Akpancar, et al. "The current perspectives of stem cell therapy in orthopedic surgery." Archives of trauma research 5(4):e37976 Dec. 2016 (Epub Aug. 2016).
Aktas E, et al. "Immune modulation with primed mesenchymal stem cells delivered via biodegradable scaffold to repair an Achilles tendon segmental defect." Journal of Orthopaedic Research 35.2; 269-280 Feb. 2017 (Epub Apr. 2016).
Anderson JD, et al. "Comprehensive proteomic analysis of mesenchymal stem cell exosomes reveals modulation of angiogenesis via nuclear factor-kappab signaling." Stem Cells;34:601-613 Mar. 2016 (Epub Feb. 2016).
Bouchlaka MN, et al. "Human Mesenchymal Stem Cell-Educated Macrophages are a Distinct High IL-6-Producing Subset that Confer Protection in Graft-versus-Host-Disease and Radiation Injury Models." Biol Blood Marrow Transplant 23: 897-905; Jun. 2017 (Epub Feb. 2017).
Chamberlain CS, et al. "Mesenchymal Stem Cell Therapy on Tendon/Ligament Healing." J Cytokine Biol 2; Jun. 2017 (Epub Jan. 2017).
Depres-Tremblay G, et al. "Rotator cuff repair: A review of surgical techniques, animal models, and new technologies under development." J Shoulder Elbow Surg; 25:2078-2085; Dec. 2016 (Epub Aug. 2016).
Eslani M, et al. "Cornea-derived mesenchymal stromal cells therapeutically modulate macrophage immunophenotype and angiogenic function." Stem Cells; May 2018 (Epub Jan. 2018).
Gomez-Aristizabal A, et al. "A systematic study of the effect of different molecular weights of hyaluronic acid on mesenchymal stromal cell-mediated immunomodulation." PLoS One;11:e0147868; Jan. 2016.
Leong DJ, et al. "Mesenchymal stem cells in tendon repair and regeneration: Basic understanding and translational challenges" Ann N Y Acad Sci; 1383:88-96; Nov. 2016 (Epub Oct. 2016).
Muir P, et al. "Autologous bone marrow-derived mesenchymal stem cells modulate molecular markers of inflammation in dogs with cruciate ligament rupture" PLoS One; 11:e0159095; Aug. 2016.
Murray PJ. "Macrophage polarization" Annu Rev Physiol; 79:541-566; Feb. 2017 (Epub Oct. 2016).
Qi X, et al. "Exosomes secreted by human-induced pluripotent stem cell-derived mesenchymal stem cells repair critical-sized bone defects through enhanced angiogenesis and osteogenesis in osteoporotic rats" Int J Biol Sci; 12:836-849; May 2016.
Saether EE et al. "Primed Mesenchymal Stem Cells Alter and Improve Rat Medial Collateral Ligament Healing" Stem Cell Rev.; 12(1):42-53; Apr. 2016 (Epub Feb. 2016).
Selleri S, et al. "Human mesenchymal stromal cell-secreted lactate induces m2-macrophage differentiation by metabolic reprogramming" Oncotarget; 7:30193-30210; May 2016.
Shen H, et al. "The effect of mesenchymal stromal cell sheets on the inflammatory stage of flexor tendon healing" Stem Cell Research & Therapy; 7: 144; (Epub Sep. 2016).
Zhang S., et al. "Exosomes derived from human embryonic mesenchymal stem cells promote osteochondral regeneration" Osteoarthritis Cartilage; 24:2135-2140; Dec. 2016 (Epub Jul. 2016).
Herzog, M. M., et al. "Trends in incidence of ACL reconstruction and concomitant procedures among commercially insured individuals in the United States, 2002-2014" Sports health; 10.6: 523-531; Nov. 2018 (Epub Oct. 2018).

\* cited by examiner

MACROPHAGE CELL THERAPY TO TREAT ORTHOPEDIC INJURY

CROSS-REFERENCE TO RELATED APPLICATIONS

This application claims the benefit of U.S. Provisional Application No. 62/581,128, filed Nov. 3, 2017, and incorporated by reference herein as if set forth in its entirety.

BACKGROUND

Tendon injuries are common occurrences with an estimated 18 Achilles tendon ruptures and 33 flexor tendon injuries per 100,000 people. In 2006, there were over 270,000 rotator cuff surgical repairs (ref Jain) performed in the US. Tendon injuries are debilitating. Aside from reducing patient quality of life, treatments are costly and re-rupture rates and poor functional outcomes can be unacceptably high. In addition to these degenerative and traumatic pathologies, orthopedic reconstructions frequently require cutting, lengthening, or transferring tendons. Regardless of whether a surgical procedure is reparative or reconstructive, the subsequent tendon healing process involves a complex, coordinated series of events that fails to regenerate the composition and mechanical properties of native tissue. Despite new surgical techniques and other therapies to improve healing and/or minimize fibrosis, the quality and speed of repair remains problematic. Typically, the neo-tendinous tissue following these repairs is functionally inferior to native tissue. The prolonged healing process requires extended periods of immobilization, causing function deficits that extend recovery even longer. Tendon injuries then result in extensive lost time from work and sports, and can impact many activities of daily living.

It is widely understood that most inflammatory cells have deleterious effects in the treatment of orthopedic injury. Additionally, administration of macrophages to treat wounds has been shown to be unsuccessful (Jetten et al., 2014 "Wound administration of M2-polarized macrophages does not improve murine cutaneous healing responses").

Although various categories of classification have been proposed, macrophages are typically divided into classically-activated (M1) and alternatively-activated (M2) macrophages. (Martinez et al., Annu. Rev. Immunol. 27:451-483 (2009)). Generally, M1 macrophages are pro-inflammatory scavenger cells that are active at times of infection and tissue injury and exhibit potent anti-microbial properties, reminiscent of type 1 T-helper lymphocyte (Th1) responses. Markers of M1 human macrophages include, but are not limited to, CD86 and HLA-DR. In contrast, M2 macrophages, also called alternatively-activated macrophages, are anti-inflammatory, pro-angiogenic, and pro-regenerative "healing" cells that promote type 2 T-helper lymphocyte (Th2)-like responses, secrete less pro-inflammatory cytokines, and assist resolution of inflammation by trophic factor synthesis and phagocytosis. (Mosser et al., Nature Rev. 8:958-969 (2008)). Markers of human M2 macrophages include, but are not limited to, CD163, CD206 and PD-L1. M2 macrophages can be further divided into subclasses (e.g., M2a, M2b, M2c, and M2d) defined by specific cytokine profiles. (Mantovani et al., Trends Immunol. 25:677-686 (2004)). While M2 macrophages are generally characterized by low production of pro-inflammatory cytokines, such as IL-12, and high production of anti-inflammatory cytokines such as IL-10, M2b macrophages can retain high levels of inflammatory cytokine production, such as TNF-α. (Mosser, J. Leukocyte Biol. 73:209-212 (2003)).

Macrophages can be polarized by their microenvironment to assume different phenotypes associated with different stages of inflammation and healing. (Stout et al., J. Immunol. 175:342-349 (2005)) and can undergo phenotypic changes in their sub-type from microenvironmental signaling. Certain macrophages are indispensable for wound healing. They participate in the early stages of cell recruitment and tissue defense, as well as the later stages of tissue homeostasis and repair. (Pollard, Nature Rev. 9:259-270 (2009)). Macrophages derived from peripheral blood monocytes have been used to treat refractory skin ulcers. (Danon et al., Exp. Gerontol. 32:633-641 (1997); Zuloff-Shani et al., Transfus. Apher. Sci. 30:163-167 (2004).)

SUMMARY OF THE INVENTION

In a first aspect, provided herein is a method of treatment to alleviate an orthopedic injury in a subject in need thereof, the method comprising the step of administering to the subject a population of cells selected from the group consisting of bone marrow exosome educated macrophages (BM-EEM) and tendon exosome educated macrophages (tendon-EEM). In some embodiments, the BM-EEM in the population are CD206 high, PD-L1 high, PD-L2 high, TGF-β high, TNF-α low, IL-6 high, and Serpine-1 high. In some embodiments, the tendon-EEM in the population are eotaxin low, TGF-α low, and IL-13 low.

In some embodiments, the population of cells is administered by injection. In some embodiments, the population of cells is administered by injection with a pharmaceutically acceptable carrier. In some embodiments, the population of cells is administered surgically.

In some embodiments, the orthopedic injury is selected from the group consisting of a partial tendon tear, a complete tendon tear, a partial tendon laceration, a compete tendon laceration, a partial tendon avulsion, a complete tendon avulsion, a partial ligament tear, a complete ligament tear, a partial ligament laceration, a compete ligament laceration, tendinopathy, tendinosis, tendinitis, meniscal tears, joint capsule tears. In some embodiments, the orthopedic injury is selected from the group consisting of plantar fasciitis, tennis elbow, bicep tendinitis, and carpal tunnel syndrome.

In some embodiments, the population of BM-EEM is generated by a method comprising the step of co-culturing a $CD14^+$ cell with bone marrow derived mesenchymal stem cells or extracellular factors derived therefrom in vitro until the $CD14^+$ cell acquires an anti-inflammatory macrophage phenotype. In some embodiments, the extracellular factor is derived from bone marrow or bone marrow derived mesenchymal stem cells. In some embodiments, the extracellular factor is selected from the group consisting of exosomes, micro-vesicles and extracellular matrix. In some embodiments, the $CD14^+$ cell is a monocyte. In some embodiments, the monocyte is obtained from the subject by leukapheresis. In some embodiments, the subject is first treated with a mobilizing agent prior to leukapheresis. In some embodiments, the mobilizing agent is selected from the group consisting of G-CSF, GM-CSF, and plerixafor.

In some embodiments, the population of cells is administered at a dose between about $1 \times 10^4$ cells/kilogram and about $10 \times 10^9$ cells/kilogram of body weight of the subject for the treatment of the orthopedic injury.

In some embodiments, the population of tendon-EEM is generated by a method comprising the step of co-culturing a CD14+ cell with tendon derived mesenchymal stem cells or extracellular factors derived therefrom in vitro until the CD14+ cell acquires an anti-inflammatory macrophage phenotype. In some embodiments, the extracellular factor is derived from tendon or tendon derived mesenchymal stem cells. In some embodiments, the extracellular factor is selected from the group consisting of exosomes, microvesicles and extracellular matrix. In some embodiments, the $CD14^+$ cell is a monocyte. In some embodiments, the monocyte is obtained from the subject by leukapheresis. In some embodiments, the subject is first treated with a mobilizing agent prior to leukapheresis. In some embodiments, the mobilizing agent is selected from the group consisting of G-CSF, GM-CSF, and plerixafor.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

The invention will be better understood and features, aspects, and advantages other than those set forth above will become apparent when consideration is given to the following detailed description thereof. Such detailed description makes reference to the following drawings.

FIG. 1A shows culture expansion of bone marrow MSCs. Exosomes were then isolated from the MSCs via ultracentrifugation. CD14+ monocytes were obtained from human peripheral blood. Monocytes were cultured, activated to CD14+ macrophages, and then exposed/educated to exosomes for 3 days, producing EEMs. Graphs show mean fluorescence intensity (MFI; FIG. 1B) and percent cells (% Cells, FIG. 1C). The surface marker, PD-L1 was significantly higher in exosome educated macrophages (EEMs) compared to the control macrophages as indicated by MFI (FIG. 1B) and % Cells (FIG. 1C). * indicates within a graph, that PBS control macrophages are different from the EEMs (results of Fisher's LSD post-hoc pairwise analysis, p<0.05). FIGS. 1D and 1E compare the flow cytometry results of EEMs from exosomes isolated from either BM-MSCs (BM-EEM) or tendon MSCs (tendon-EEM) as indicated by MFI (FIG. 1D) and percent cells (% cells, FIG. 1E). Results are expressed as mean±S.E.M.

FIGS. 4G-4J show representative images of type I collagen by the day 14 Achilles tendon after (FIG. 4G) HBSS (control), (FIG. 4H) MSC, (FIG. 4I) MQ, or (FIG. 4J) EEM treatment. Bars without a common superscript letter within a graph are significantly different (results of Fisher's LSD post-hoc pairwise analysis, p<0.05). Values are expressed as mean density±S.E.M.

DETAILED DESCRIPTION OF THE INVENTION

Figures 1A, 1B, 1C, 1D, 1E:
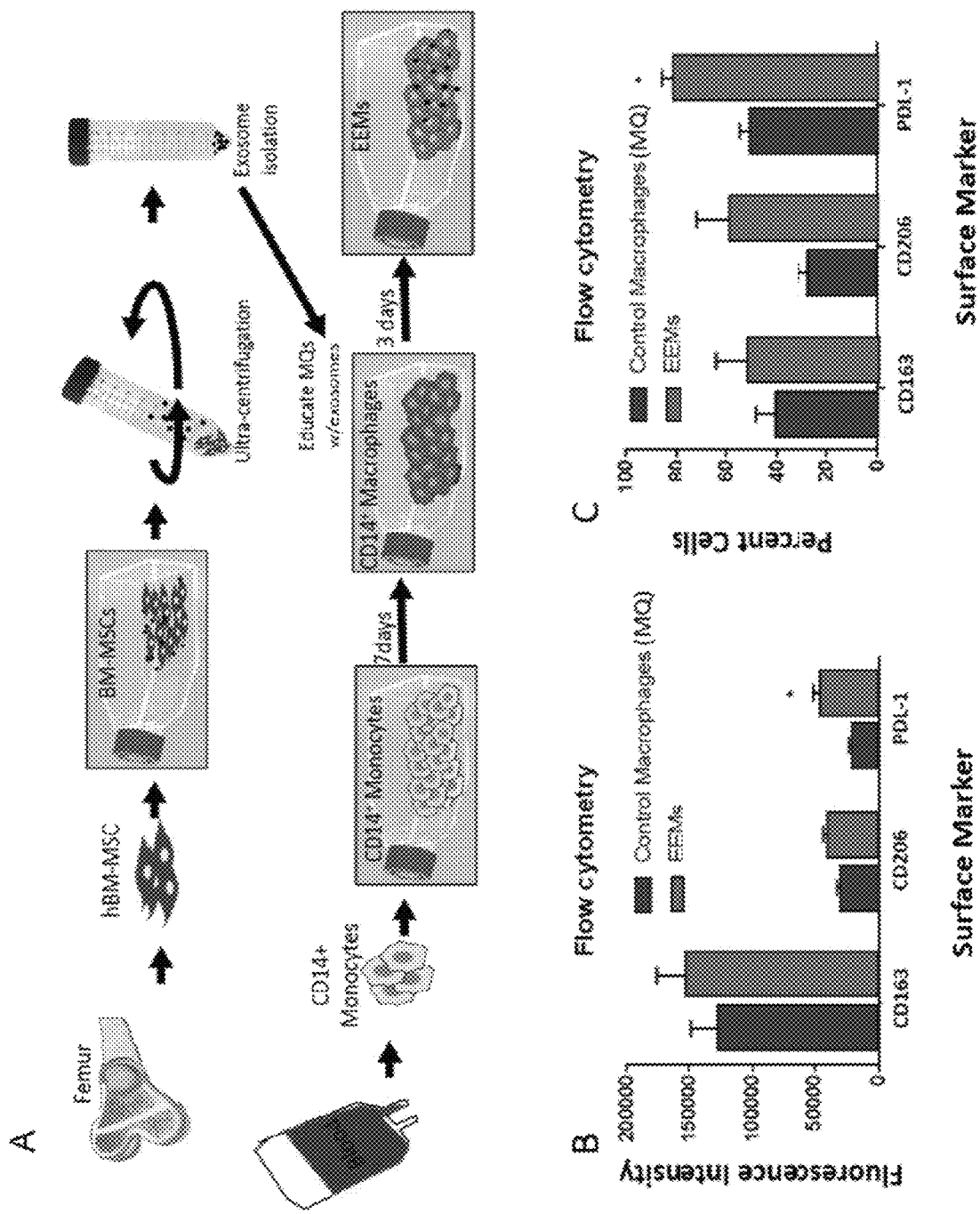
FIGS. 1A-1E show fabrication and characterization of EEMs generated from human CD14+ cells derived from a single patient.
Figures 1A, 1B, 1C, 1D, 1E:
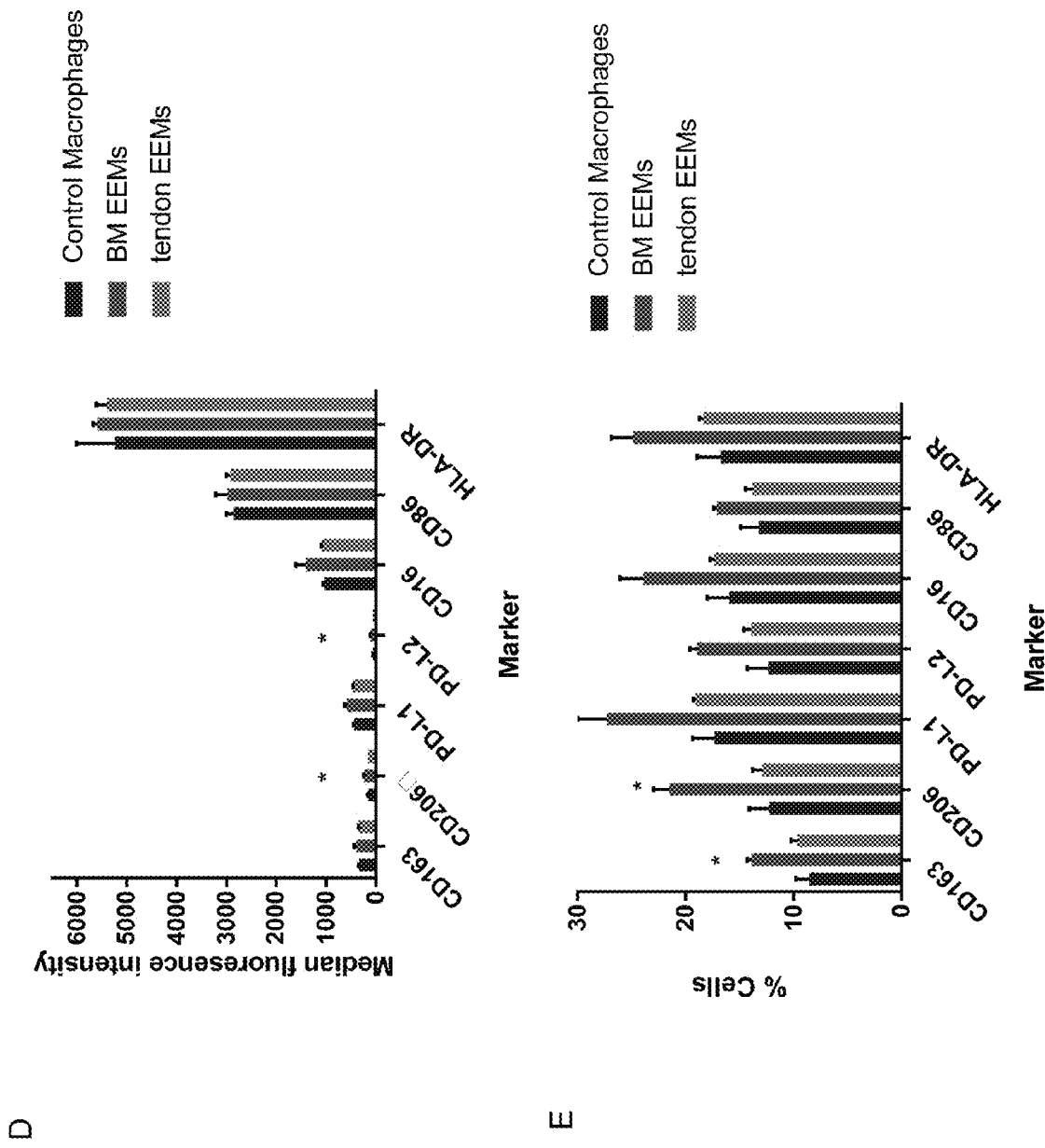

The present disclosure broadly relates to tissue-specific educated macrophages as well as methods for making and using such a macrophage in the treatment of orthopedic injury.

In one aspect of the invention, $CD14^+$ monocytes or macrophages are co-cultured with tissue-specific cells or extracellular factors to yield tissue-specific educated macrophages. Educated macrophages generated by the methods of the present invention may be used to treat and prevent orthopedic injury by administration of the educated macrophages to a subject in need thereof. In some embodiments, the tissue specific cells are mesenchymal stem cells (MSCs) isolated from bone marrow (BM), tendons, or adipose. In some embodiments, the extracellular factors are microvesicles, exosomes, extracellular matrix (ECM), or extracellular vesicles (EV) isolated from the tissue specific cells.

As used herein, "educated macrophage" refers to tissue-specific anti-inflammatory and tissue reparative macrophages generated ex vivo by co-culturing a $CD14^+$ monocyte or macrophage with a tissue-specific cell or with an extracellular factor. In one embodiment, the educated macrophages are specific to bone marrow cells and are generated by co-culturing $CD14^+$ monocytes or macrophages with bone-marrow-specific cells or extracellular factors. In one embodiment, educated macrophages are generated by co-culture of bone-marrow MSC derived exosomes with CD14+ monocytes and are generally characterized as CD14+, CD206 high, PD-L1 high, PD-L2 high, TGF-β high, IL-6 high, and TNF-α low, when averaged from multiple human isolates compared to non-educated macrophages.

Co-Culture $CD14^+$ cells are co-cultured with cells from a specific tissue ("tissue-specific cells") or with extracellular factors to yield educated macrophages. Methods of co-culturing $CD14^+$ cells with mesenchymal stem cells (MSCs) to generate MSC-educated macrophages (referred to herein as BM-MEM) have been described, see U.S. Pat. No. 8,647,678 and U.S. Patent Publication No. 2016/0082042, both incorporated herein by reference. Additional methods of co-culturing CD14+ cells with tissue-specific cells or extracellular factors have been described, see U.S. Patent Publication No. 2018/0282698, which is incorporated herein by reference. In some embodiments, $CD14^+$ cells are co-cultured with both tissue-specific cells and extracellular factors.

CD14+ cells are co-cultured ex vivo with tissue-specific cells or extracellular factors in any culture medium known in the art suitable for survival and growth of the co-culture components. The co-cultures may be maintained for between 0-20 days to generate educated macrophages. Co-cultures may generate educated macrophages with the desired immuno-phenotype after 1, 2, 3, 4, 5, 6, 7, 8, 9, 10, 11, 12, 13, 14, or more than 15 days. In some embodiments, co-cultures yield educated macrophages after 10 days. In some embodiments, co-cultures yield educated macrophages after 5 days. In one embodiment, co-cultures yield educated macrophages after 1 day.

In some cases, tissue-specific cells or extracellular factors are subjected to additional purification steps prior to use in co-culture to generate educated macrophages. Tissue-specific cells or extracellular factors can be added in a single dose or repeated doses to $CD14^+$ cultures to generate educated macrophages.

For co-cultures of the present invention, $CD14^+$ monocytes or macrophages can be co-cultured with tissue-specific cells or extracellular factors such that the cells are in direct physical contact. Alternatively, the co-culture components can be placed in sub-compartments that are in fluid communication but separated by a semi-permeable membrane. The semi-permeable membrane allows the exchange of soluble medium components and factors secreted by the cells but is impenetrable for the cells themselves. The pores within the semi-permeable membrane are sufficiently small to prevent cell penetration but large enough to allow soluble medium components to pass across the membrane, and are typically are between 0.1-1.0 μm, but other pore sizes can be suitable.

Various methods of cell separation and isolation are known in the art and can be used to separate the educated macrophages from the tissue-specific cells and extracellular factors depending on factors such as the desired purity of the isolated cell populations. For example, educated macrophages can be isolated from the co-culture using flow cytometry or magnetic based sorting. Educated macrophages can be maintained in culture in any medium that supports macrophages in vitro. Also, educated macrophages can be stored using methods known in the art including, but not limited to, refrigeration, cryopreservation, vitrification, and immortalization.

As used herein, "$CD14^+$ cell" refers to a monocyte or a macrophage. $CD14^+$ cells can be derived from any suitable source. The skilled artisan will appreciate the advantageous efficiency of generating macrophages from peripheral blood monocytes for co-cultures. Alternatively, macrophages can also be isolated from cellular outgrowth of a tissue sample taken from an individual. In some embodiments, the sample can be a bone marrow sample. Peripheral blood monocytes can be cultured for various times and under various conditions before exosomes or extracellular factors are added for co-cultures. In some embodiments, CD14+ cells are added directly to co-cultures. In one embodiment, monocytes are harvested from a subject by leukapheresis. In one embodiment, CD14+ cells are isolated from peripheral blood. In one embodiment, CD14+ cells are isolated from peripheral blood of a patient who has first been treated with an agent including but not limited to granulocyte-colony stimulating factor (G-CSF), granulocyte-macrophage colony-stimulating factor (GM-CSF), MOZOBIL™ (plerixafor) and the like to mobilize cells into the peripheral blood. In one embodiment, CD14+ cells are isolated from peripheral blood with G-CSF stimulation. In one embodiment CD14+ cells are isolated from bone marrow aspirates. In one embodiment CD14+ cells are isolated from tissues or organs. In one embodiment CD14+ cells are derived from pluripotent stem cells such as embryonic stem cells or induced pluripotent stem cells.

As used herein "macrophage" refers to a mononuclear phagocyte characterized by the expression of CD14 and lack of expression of dendritic or mesenchymal cell markers.

As used herein "mononuclear leukocytes" or "monocytes" are white blood cells that can differentiate into macrophages when recruited to tissues and can influence both innate and adaptive immune system.

As used herein, "high" means that the cells are characterized by higher expression of a particular cytokine compared to control macrophages cultured without tissue-specific cells or extracellular factors. For example, "IL-6 high" indicates that macrophages co-cultured with tissue-specific cells or extracellular factors express higher amounts of IL-6 than macrophages that have not been co-cultured with tissue-specific cells or extracellular factors. Similarly, "low" means that the cells are characterized by lower expression of a particular cytokine. For example, "IL-12 low" indicates that macrophages co-cultured with tissue-specific cells or extracellular factors express lower amounts of IL-12 than macrophages that have not been co-cultured with tissue-specific cells or extracellular factors. "Low" can also mean that the expression levels are below the detection limit.

Tissue-Specific Cells and Extracellular Factors

The skilled artisan will appreciate that monocytes, macrophages, tissue-specific cells, and extracellular factors employed in methods described herein can be cultured or co-cultured in any medium that supports their survival and growth. In some embodiments, the medium is cell growth medium such as alpha MEM or RPMI-1640 with bovine serum or human serum depleted of exosomes by methods such as ultracentrifugation. In some embodiments, the medium is serum free-medium including but not limited to X-VIVO™ 15 and STEMPRO™ serum-free media. In one embodiment the medium uses human platelet lysates to replace the human AB serum in the macrophage medium. Co-cultures do not require the addition of cytokines. Tissue-specific cells, extracellular factors and macrophages can be autologous, syngeneic, allogeneic, xenogenic, or third party with respect to one another. Tissue-specific cells, extracellular factors and macrophages can be pluripotent stem cell derived.

As used herein, "mesenchymal stem cells (MSC)" refers to the fibroblast-like cells that reside within virtually all tissues of a postnatal individual. An ordinarily skilled artisan will appreciate that the cells referred to herein as mesenchymal stem cells or MSCs are also known in the art as mesenchymal stromal cells, marrow stromal cells, multipotent stromal cells, and perhaps by other names. An MSC within the scope of this disclosure is any cell that can differentiate into osteoblasts, chondrocytes, tenocytes, myoblasts, astrocytes, and adipocytes. An MSC within the scope of this disclosure is positive for the expression of CD105, CD73, and CD90 while lacking expression of CD45, CD34, CD14 or CD11b, CD79α or CD19, and HLA-DR surface molecules. (Dominici et al. Minimal criteria for defining multipotent mesenchymal stromal cells. The International Society for Cellular Therapy position statement, (2006), Cytotherapy, 8(4):315-317). While these markers are known to characterize MSCs derived from most tissues, it is understood in the art that MSCs from some sources could exhibit differences in cell surface marker expression. Within bone marrow, MSCs provide the stromal support tissue for hematopoietic stem cells. MSCs can differentiate into cells of the mesenchymal lineage. In some embodiments, MSCs are co-cultured with CD14$^+$ cells to generate MSC educated macrophages (referred to herein as MEMs).

In some embodiments of the present invention the tissue-specific cells are bone marrow mesenchymal stem cells (referred to herein as BM-MSCs). BM-MSCs are co-cultured with CD14$^+$ cells to generate bone marrow specific educated macrophages (referred to herein as BM-MEM).

In some embodiments of the present invention the tissue-specific cells are MSCs derived from non-bone marrow tissues such as tendon, ligament, muscle, other connective tissues, or adipose.

MSCs, BM-MSCs, tendon-MSCs, adipose-MSCs and other cells described herein for use in the methods or compositions of the present invention may be derived or isolated from any suitable source. In one embodiment, MSCs are isolated from tissue such as bone marrow, ligament, adipose, and tendon tissue. In one embodiment, MSCs are differentiated from embryonic or induced pluripotent stem cells.

As used herein, "extracellular factors" refers to extracellular vesicles, exosomes, micro-vesicles, extracellular matrix compositions, isolated extracellular matrix components and fragments or derivatives thereof, exosomes purified from an extracellular matrix, and combinations thereof. Extracellular factors are used in co-culture with CD14$^+$ cells to educate macrophages in a tissue-specific manner. As used herein, "extracellular vesicles" refers to both exosomes and micro-vesicles.

As used herein, "exosomes" refer to small lipid vesicles released by a variety of cell types. Exosomes are generated by inward- or reverse budding, resulting in particles that contain cytosol and exposed extracellular domains of certain membrane-associated proteins (Stoorvogel et al., *Traffic* 3:321-330 (2002)). Methods of preparing exosomes from cells are known in the art. See, for example, Raposo et al., *J. Exp. Med.* 183:1161 (1996). In one method, exosomes are recovered from conditioned culture medium by centrifugation. In some embodiments of the invention, exosomes are co-cultured with macrophages to generate tissue-specific educated macrophages with increased specificity for the tissues from which the exosomes were derived. Exosomes suited for use in the methods can be derived fresh or can be frozen aliquots kept as a composition, thawed, and added in a single dose or repeated doses to CD14$^+$ cultures to generate educated macrophages. In some embodiments, exosome preparations may also include micro-vesicles. Without wishing to be bound by any particular theory, it is understood that tissue specific exosomes are known to express surface markers or contain DNA, RNA, microRNA, or proteins specific to their tissue of origin which may result in tissue-specific educated macrophages that are targeted to the tissue of origin. Exosomes from a tissue of interest, for example, a damaged tissue targeted for repair, are likely to contain tissue-specific translational or post-translational factors, internal nucleic acids, and proteins specific to the tissue of interest and superior for repair of said tissue.

Exosomes can have, but are not limited to, a diameter of about 10-300 nm. In some embodiments, the exosomes can have, but are not limited to, a diameter between 20-250 nm, 30-200 nm or about 50-150 nm. Exosomes may be isolated or derived from any cell type present in a target tissue of interest and cultured for a period of time and under conditions appropriate for the isolation of exosomes.

In some embodiments, the exosomes are derived from bone marrow mesenchymal stem cells. Exosomes derived from bone marrow MSCs are co-cultured with CD14$^+$ cells to generate bone marrow exosome-educated macrophages (referred to herein as BM-EEM) with an anti-inflammatory phenotype. When comparing external surface markers of MEMs to BM-EEMs by flow cytometry averaged from multiple human CD14+ isolates, the BM-EEMs are CD163 and CD16 low and CD206, PDL-1, and PDL-2 high. When comparing gene expression by qPCR averaged over multiple isolates, BM-EEMs are TGF-β, TNF-α, and IL-1β high and IL-6, serpine-1 and VEGF low compared to the MEMs.

Characteristic surface marker phenotypes and cytokine growth factor profiles of some embodiments of the educated macrophages described herein are outlined in Table 1:

| Educated Macrophage | Surface marker phenotype determined by flow cytometry averaged over multiple CD14+ isolates | Cytokine, growth factor profile determined by qPCR averaged over multiple CD14+ isolates | As compared to |
|---|---|---|---|
| MEM | CD163 high, CD206 high, CD16 high | TGF-β low, TNF-α low, IL-6 very high, IL-10 low, IL-1b low, VEGF-A high, Serpine-1 high | Un-educated macrophages |
| BM-EEM | CD163 low, CD206 high, CD16 low, PD-L1 high, PD-L2 high | TGF-β high, TNF-α low, IL-6 high, IL-1β high, Serpine-1 high | Un-educated macrophages |
| BM-EEM | CD163 low, CD206 high, CD16 low, PD-L1 high, PD-L2 high | TGF-β high, TNF-α high, IL-6 low, IL-10 high, FGF-2 low, IL-1β high, VEGF-A low, VEGF-C low, Serpine-1 low | MEM |

In some embodiments, the exosomes are derived from tendon mesenchymal stem cells. Exosomes derived from tendon MSCs are co-cultured with CD14$^+$ cells to generate tendon exosome-educated macrophages (referred to herein as tendon-EEMs) with an anti-inflammatory phenotype. When comparing the secretion profile of chemokines and cytokines, tendon-EEMs secreted significantly lower levels of IL-13 than control macrophages. Compared to BM-EEMs, the tendon-EEMs secreted significantly lower IL-13, eotaxin, INFa2, and TGF-α.

Treatment

According to the methods of the present invention, educated macrophages are administered to a subject in need thereof. Subjects in need of treatment include those already having or diagnosed with a disease or injury as described herein or those who are at risk of developing a disease or injury as described herein.

A disease or injury of the present invention may include, but is not limited to, conditions associated with an orthopedic or traumatic injury. Orthopedic injury may refer to, but is not limited to, partial or complete tendon or ligament tears, partial or complete tendon or ligament lacerations, partial or complete tendon or ligament avulsions, tendinopathy, tendinosis, tendinitis, meniscal tears, and joint capsule tears. Additional conditions associated with orthopedic injury include, but are not limited to, plantar fasciitis, tennis elbow, bicep tendinitis, carpal tunnel syndrome, repetitive motion injuries (e.g., iliotibial band), non-surgically repaired ligament injuries, non-surgically repaired tendon injuries. The tendon or ligament at risk of or affected by the orthopedic injury may be any tendon or ligament known in the body of a given subject. Diseases or injuries associated with orthopedic injury may affect, but are not limited to, injuries of the Achilles tendon, rotator cuff tendons (supraspinatus, infraspinatus, subscapularis, teres minor), biceps tendon, anterior cruciate ligament, posterior cruciate ligament, medial collateral ligament, lateral collateral ligament, flexor tendons, extensor tendons, knee meniscus, shoulder labrum, hip labrum, joint capsule, patellar tendon, hamstring tendons, retinacula (e.g. flexor retinacula creating carpal tunnel), aponeuroses, tendon/ligament enthuses.

As used herein, the terms "treat" and "treating" refer to both therapeutic and prophylactic or preventive measures, wherein the object is to prevent or slow down (lessen) an undesired physiological change or pathological disorder resulting from a disease or injury as described herein. For purposes of this invention, treating the disease or injury includes, without limitation, alleviating one or more clinical indications, decreasing inflammation, reducing the severity of one or more clinical indications of the disease or injury, diminishing the extent of the condition, stabilizing the subject's disease or injury (i.e., not worsening), delaying or slowing, halting, or reversing the disease or injury and bringing about partial or complete remission of the disease or injury. Treating the disease or injury also includes reducing the recovery time required before return to activity by days, weeks, months, or years as compared to prognosis if treated according to standard medical practice not incorporating treatment with educated macrophages.

Subjects in need of treatment can include those already having or diagnosed with a disease or injury as described herein as well as those prone to, likely to develop, or suspected of having a disease or injury as described herein. Pre-treating or preventing a disease or injury according to a method of the present invention includes initiating the administration of a therapeutic (e.g., human educated macrophages) before the disease or injury appears or exists, or before a subject is exposed to factors known to induce the disease or injury. Pre-treating the disorder is particularly applicable to subjects at risk of having or acquiring the disease or injury. As used herein, the terms "prevent" and "preventing" refer to prophylactic or preventive measures intended to inhibit undesirable physiological changes or the development of a disorder or condition resulting in the disease or injury. In exemplary embodiments, preventing the disease or injury comprises initiating administration of a therapeutic (e.g., educated macrophages) at or before the appearance or existence of the disease or injury, such that the disease or injury, or its symptoms, pathological features, consequences, or adverse effects do not occur. In such cases, a method of the invention for preventing the disease or injury comprises administering educated macrophages to a subject in need thereof prior to exposure of the subject to factors that influence the development of the disease or injury.

As used herein, the terms "subject" or "patient" are used interchangeably and can encompass any vertebrate including, without limitation, humans, non-human primates, mammals, reptiles, amphibians, birds, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease or injury as described herein or a pathological symptom or feature associated with a disease or injury as described herein.

In some cases, a method of treating or preventing a disease or injury as described herein comprises administering a pharmaceutical composition comprising a therapeutically effective amount of educated macrophages as a therapeutic agent (i.e., for therapeutic applications). As used herein, the term "pharmaceutical composition" refers to a chemical or biological composition suitable for administration to a mammal. Examples of compositions appropriate for such therapeutic applications include preparations for parenteral, subcutaneous, transdermal, intradermal, intramuscular, intravenous (e.g., injectable), intrajoint, intratendon, intraligament, intrasynovial, extrasynovial, or intratracheal administration, such as sterile suspensions, emulsions, and aerosols. In some cases, pharmaceutical compositions appropriate for therapeutic applications may be in admixture with one or more pharmaceutically acceptable excipients, diluents, or carriers such as sterile water, physiological saline, glucose or the like. For example, educated macrophages described herein can be administered to a subject as a pharmaceutical composition comprising a carrier solution.

Formulations may be designed or intended for oral, rectal, nasal, topical or transmucosal (including buccal, sublingual, ocular, vaginal and rectal) and parenteral (including subcutaneous, intramuscular, intravenous, intradermal, intraperitoneal, intrathecal, and epidural) administration. As used herein, "topical" administration is intended to include administration directly to the tendon, ligament, or site of injury of the subject. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy*, 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, educated macrophages may be optionally administered in combination with one or more additional active agents. Such active agents include anti-inflammatory, anti-cytokine, analgesic, antipyretic, antibiotic, and antiviral agents, as well as growth factors and agonists, antagonists, and modulators of immunoregulatory agents (e.g., TNF-$\alpha$, IL-2, IL-4, TGF$\beta$, IL-6, IL-10, IL-12, IL-13, IL-17, IL-18, IFN-$\alpha$, IFN-$\gamma$, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Any suitable combination of such active agents is also contemplated. When administered in combination with one or more active agents, educated macrophages can be administered either simultaneously or sequentially with other active agents. For example, victims of orthopedic injury may simultaneously receive educated macrophages and a steroid or corticosteroid for a length of time or according to a dosage regimen sufficient to support recovery and to treat, alleviate, or lessen the severity of the orthopedic injury.

In some embodiments, educated macrophages of the present invention may also be administered to a patient simultaneously undergoing surgical or endoscopic repair of the orthopedic injury. In such cases, educated macrophages can be provided to a subject in need thereof in a pharmaceutical composition adapted for direct administration to the tendon or ligament. Administration may be provided before, after or simultaneous with repair and suture of the tendon or ligament. Surgery of ACLs, for example, is typically delayed to allow initial inflammation to subside. Without being bound by any particular theory, administration of EEMs to the subject could speed the process of reducing inflammation, shorten the time between injury and surgical treatment, initiate healing, and reduce injury-induced joint inflammation (associated with increased osteoarthritis in injured joints). Post-surgery administration of EEMs would reduce surgically induced complications associated with inflammation, angiogenesis, fibrosis, and degradation of repaired or replaced tissues as well as peri-ligamentous or peri-tendonous tissues (e.g. cartilage). EEMs can be administered directly to the tendon or ligament being repaired. EEMs may also be administered as part of a treatment in which the subject is receiving donor or graft tissues. EEMs may be applied via a collagen sponge or gel, hydrogel, or tissue engineered scaffold. Administration as part of a cell sheet or sheath around the tendon or ligament being treated is also envisioned.

In some embodiments, educated macrophages are administered to a subject in need thereof using an infusion, topical application, surgical transplantation, or implantation. In an exemplary embodiments, administration is systemic. In such cases, educated macrophages can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising human educated macrophages are cryopreserved prior to administration.

Therapeutically effective amounts of educated macrophages are administered to a subject in need thereof. An effective dose or amount is an amount sufficient to effect a beneficial or desired clinical result. With regard to methods of the present invention, the effective dose or amount, which can be administered in one or more administrations, is the amount of human educated macrophages sufficient to elicit a therapeutic effect in a subject to whom the cells are administered. In some cases, an effective dose of educated macrophages is about $1\times10^4$ cells/kilogram to about $10\times10^9$ cells/kilogram of body weight of the recipient. Effective amounts will be affected by various factors which modify the action of the cells upon administration and the subject's biological response to the cells, e.g., severity of the orthopedic injury, type of damaged tissue, the patient's age, sex, and diet, the severity of inflammation, time of administration, route of administration, and other clinical factors. In some embodiments, the effective dose is about $1\times10^4$ cells/kilogram to about $6\times10^9$ cells/kilogram. In one embodiment, the effective dose is about $5\times10^7$ cells/kilogram. In some embodiments, the effective dose is $1\times10^4$ cells/kilogram to about $10\times10^9$ cells/kilogram based on the weight of the tendon or ligament being treated.

Therapeutically effective amounts for administration to a human subject can be determined in animal tests and any art-accepted methods for scaling to determine an amount effective for human administration from an amount effective in an animal test. For example, an amount can be initially measured to be effective in an animal model (e.g., to achieve a beneficial or desired clinical result). The amount determined to be effective in the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the educated macrophages. For example, an educated macrophage dosage for a particular subject with an orthopedic injury can be increased if the lower dose does not elicit a detectable or sufficient improvement in the orthopedic injury. Conversely, the dosage can be decreased if the orthopedic injury is treated or eliminated.

In some cases, therapeutically effective amounts of educated macrophages can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular disease state being treated, the physical condition of the subject, the type of animal being treated, the duration of the treatment, and the nature of any concurrent therapy.

Following administration of educated macrophages to an individual subject afflicted by, prone to, or likely to develop a disease or injury described herein, a clinical symptom or feature associated with the disease or injury is observed and assessed for a positive or negative change. For example, for methods of treating orthopedic injury in a subject, positive or negative changes in the subject's recovery during or following treatment may be determined by any measure known to those of skill in the art including, without limitation, observing change in or measuring range of motion, inflammation, adhesion, edema, bulging, fibrotic tissue formation, stability, stiffness, estimated strength, pain, and compensation in musculoskeletal activities. In general, treatment of an orthopedic injury will result in one or more of an increase in range of motion, a reduction in joint stiffness, a reduction of tenderness or swelling at the site of injury, and a reduction in the estimated strength and stiffness of the effected ligament or tendon.

In some cases, the injectable composition is delivered to the tendon or ligament using any appropriate means for delivery. For example, delivery of an injectable composition described herein can be achieved using a delivery device comprising a needle and/or syringe. In one embodiment, a suitable delivery vehicle may be tissue-specific extracellular matrix. In some embodiments, the EEMs are administered as part of a tissue engineered scaffold by injector or directly as part of a surgical treatment.

In any of the methods of the present invention, the donor and the recipient of the educated macrophages can be a single individual or different individuals, for example, autologous, allogeneic or xenogeneic individuals. As used herein, the term "allogeneic" refers to something that is genetically different although belonging to or obtained from the same species (e.g., allogeneic tissue grafts or organ transplants). "Xenogeneic" means the cells could be derived from a different species.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting Examples.

Example 1

The embodiment described here demonstrates the concept that bone marrow-specific alternatively activated tissue-reparative macrophages can be bioengineered by conditioning circulating monocytes with bone marrow mesenchymal stem cell derived exosomes. We describe these macrophages as Bone Marrow Exosome-Educated Macrophages (BM-EEM). In a proof of concept in vivo study, BM-EEM were used in a mouse Achilles tendon injury model We observed a significant increase in strength and an increase in endogenous M2 production as compared to control animals and standard treatments.

Macrophage polarization, both in vitro and in vivo, can be induced by MSC paracrine activity. MSCs educate macrophages towards an anti-inflammatory phenotype (MSC-educated macrophages [MEMs]). Compared to uneducated macrophages, MEMs exhibited a unique M2-like macrophage phenotype with high IL-6 expression. In mouse models, MEMs enhanced mouse survival during lethal graft-versus-host disease and after radiation injury when compared to MSC or macrophage treatments. See US Patent Publication US 2016/0082042, which is incorporated herein by reference. Since MSCs typically require several weeks of culture to expand enough cells for potential therapeutic application, a universal allogeneic growing stock of pre-characterized MSCs from frozen cell banks is envisioned. Collection of monocytes via leukapheresis, followed by culture with a universal allogeneic MSC-produced extracellular paracrine factor could provide adequate stimulation for educating macrophages to an anti-inflammatory phenotype in a simple and clinically feasible fashion. MSCs secrete many growth factors and cytokines, but exosomes or ECM which contain proteoglycans which trap and store exosomes and growth factors provide a key paracrine signaling mechanism. Exosomes from donor cells, autologous, allogeneic or third party may be sufficient to induce a biological response in recipient cells. Exosomes also resist degradation, are easy to store, and are produced in much higher concentrations than stem cells. Therefore, use of MSC-derived exosomes to educate macrophages to create an anti-inflammatory phenotype (EEMs) provides a novel and intriguing method to polarize macrophages. Altogether, we hypothesize that the exogenous application of human MSC-derived exosome-educated macrophages (EEMs) will improve tendon healing by altering tissue inflammation and the endogenous macrophage phenotypes into a more favorable M1/M2 ratio.

Methods

Cell culture—All protocols were approved by the Health Sciences Institutional Review Board of University of Wisconsin-Madison School of Medicine and Public Health. Monocytes were isolated from human peripheral blood using magnetic bead separation methods according to manufacturers' protocols. Briefly, peripheral blood mononuclear cells were collected from the blood of healthy donors by density gradient separation using Percoll (GE Healthcare Bio-Sciences, Piscataway, N.J., USA). Red blood cells were lysed by incubating cells in ACK lysis buffer for 3 minutes and mononuclear cells were washed with phosphate-buffered saline (PBS). To reduce platelet contamination, cell suspensions were centrifuged at 300-700 rpm for 10 minutes and cell pellets were resuspended and incubated with anti-human CD14 microbeads (Miltenyi Biotech, Auburn, Calif., USA) for 15 minutes at 4° C. After washing to remove unbound antibody, cell separation was done using autoMACS™ Pro Separator (Miltenyi Biotech). Purity of isolated CD14$^+$ cells was >95% by flow cytometry. Purified CD14$^+$ monocytes were either plated into six-well culture plates at a concentration of 0.5-1×10$^6$ per well or 10$^7$ per T75 cm$^2$ filter cap cell culture flask (Greiner Bio-One, Monroe, N.C., USA) in Iscove's modified Dulbecco's media supplemented with 10% human serum blood type AB (Mediatech, Herndon, Va., USA), 1× nonessential amino acids (Lonza, Walkersville, Md., USA), 4 mM L-glutamine (Invitrogen, Carlsbad, Calif., USA), 1 mM sodium pyruvate (Mediatech), and 4 ug/mL recombinant human insulin (Invitrogen). Cells were cultured for 7 days at 37° C. with 5% $CO_2$, without adding any cytokines, to differentiate to macrophages. Attached cells were harvested using Accumax dissociation media (Innovative Cell Technologies, Inc, San Diego, Calif.).

Mesenchymal stem cells (MSCs) were isolated from filters left over after bone marrow (BM) harvest from normal healthy donors to human leukocyte antigen (HLA)-matched siblings or from dissected tendon tissue from hamstring or biceps from human donors. Briefly, for the isolation of BM MSCs, BM cells trapped in the filter were recovered by rinsing the filter with PBS and mononuclear cells were separated using FICOLL™-Hypaque 1.073 (GE Healthcare Bio-Sciences). Red blood cells were lysed with 3-minute incubation in ACK lysis buffer and mononuclear cells were suspended in α-minimum essential medium supplemented with 10% fetal bovine serum (US origin, uncharacterized; Hyclone, Logan, Utah, USA), 1× nonessential amino acids, and 4 mM L-glutamine. Cells were cultivated in 75-$cm^2$ filter cap cell culture flasks.

For the isolation of MSCs from human tendons, resected tendon samples from hamstring or bicep tissue after surgery were harvested and minced-up in a petri dish in MSC culture media containing 0.5% w/v of collagenase type 1 (from *C. histolyticum*). The sample was allowed to digest by incubation for about 18 hours at 37° C., 5% $CO_2$. This digested material was then strained through a 100 uM cell strainer to remove the clumps, collected and centrifuged at 500×g for 10 minutes. The cell pellet was re-suspended in MSC culture medium, placed in culture flasks and incubated for 18 hours to allow the MSCs to attach.

Attached cells derived from BM or tendon (passage 0) were harvested using TrypLE™ cell dissociation enzyme (Invitrogen) and then re-plated into new flasks as described previously (Kim J et al Exp Hematology (2009)). Each subsequent re-plating was considered a separate passage (P3, P4, etc.). Isolates from either BM or tendon were confirmed to be MSCs by flow cytometry as described (Dominici M et al. Cytotherapy 8(4):315-317 (2006)). After confirmation, the isolates were used for the production of extracellular vesicles (EVs).

Isolation and characterization of EV's from MSCs—MSCs isolated from either BM or tendon were grown to confluence in 75-$cm^2$ filter cap cell culture flasks then washed once with PBS, and the medium was replaced with StemPro™ MSC serum-free medium (SFM) CTS (A103332-01, Gibco Life Technologies). Cell were incubated for 18-24 hours and the conditioned culture medium (CM) was collected and EVs were isolated by ultracentrifugation essentially as described (Thery C. et al. Current Protocols in Cell Biology (2006)). The CM was centrifuged using a Beckman Coulter Allegra® X-15R centrifuge at 2000×g at 4° C. for 20 minutes to remove any detached cells, apoptotic bodies and cell debris. Clarified supernatant CM was then centrifuged in a Beckman Coulter Optima™ L-80XP Ultracentrifuge at 100,000 $g_{avg}$ at 4° C. for 2 hours with a SW 28 rotor to pellet EVs. The supernatant was carefully removed, and EV-containing pellets were re-suspended in PBS and pooled. EV pellet was resuspended at 100 ul PBS/10 mls of CM and characterized using a Thermo NanoDrop spectrophotometer for protein and RNA concentration. Particle diameter and concentration were assessed using an IZON qNano Nanoparticle Characterization instrument performed by Zenbio Inc., Research Triangle Park, N.C.

Education of macrophages to M2-like phenotype using EV's from MSCs—Macrophages were educated by EVs isolated from the MSCs isolated from BM or tendon. In the experiments described, EVs were added to macrophages on day 7 then educated by cultivation for 3 days to produce EEMs. It is also possible to co-culture the EVs and macrophages for between 3-7 days. Macrophages were educated to produce EEM's in 75-$cm^2$ filter cap cell culture flasks (10 mls) using approximately $3 \times 10^{10}$ exosomes per flask of cells. Control macrophages were treated with PBS. The macrophages were harvested by removing media, washing with phosphate-buffered saline (PBS) then using ACCUMAX™ cell dissociation enzyme (Innovative Cell Technologies, Inc) to detach the cells from the flask followed by the use of a cell scraper. A small portion of the control macrophages and EEMs were analyzed by flow cytometry and the remainder was for the animal studies.

Flow cytometry—Control macrophages or BM-EEMs at day 10 of culture were collected, counted and incubated with Fc block (BD Pharmingen, cat: #564220) and stained for surface markers at 4° C. for 20-30 minutes with anti-human antibodies including PerCP/Cy5.5-CD14 (HCD14, cat #325622), a macrophage surface marker and three M2 markers; FITC-CD163 (GHI/61, cat #333618), PE-CD206 (15-2, cat #321106), and APC-PD-L1 (29E.2A3, cat #329708). All antibodies were purchased from BioLegend (San Diego, Calif.). Compensation was achieved using Ultra-comp beads (cat #01-2222-42, e-bioscience). CD14 positive cells were evaluated for the presence of M2 markers by determining the Median Fluorescence Intensity (MFI) of the cells and % cells stained. The flow profile was also determined for tendon-EEMs at day 10 of culture and compared to control macrophages and BM-EEMs. In addition to the surface markers described above, surface markers analyzed induce macrophage marker, BV421-CD16 (3G8, cat #302038), M2 marker APC-PD-L2 (24F.10C12, cat #329608), and M1 markers, BV510-CD86 (IT2.2, cat #305432) and Pacific Blue-HLA-DR/MHC II (L234, cat #307633) were analyzed. Flow cytometry data were acquired on an ACCURI™ C9 cell analyzer (BD Biosciences, San Jose Calif.) or MACSQuant analyzer 10 (Miltenyi Biotec).

Cytokine, chemokine, and growth factor multiplex ELISA—Day 10 macrophage controls (untreated), BM-EEMs and tendon-EEMs ($10^6$/well) in 6-well plates were washed with PBS, replaced with culture medium, and incubated for 24 hours. The culture medium was recovered, centrifuged at 300×g for 10 minutes to remove any floating cell debris and assayed for secreted factors using a Milliplex MAP cytokine/chemokine multiplex magnetic bead panel (HCYTOMAG-60K, Millipore, Burlington Mass.), including epidermal growth factor (EGF), fibroblast growth factor (FGF-2), EOTAXIN, Transforming growth factor beta (TGF-a), granulocyte-colony stimulating factor (G-CSF), FMS-like tyrosine kinase 3 ligand (FLT-3L), granulocyte-macrophage colony-stimulating factor (GM-CSF), chemokine (C—X3-C motif) ligand 1 (FRACTALKINE), interferon alpha 2 (INFa2), interferon-gamma (IFNg), growth related oncogene (GRO), C—C motif chemokine 22 (MDC), platelet-derived growth factor (PDGF-BB), Soluble CD40 ligand (sCD40L), interleukins and interleukin subunits, IL-1ra, IL-1a, IL-1b, IL-2, IL-4, IL-5, IL-6, IL-7, IL-8, IL-9 IL-10, IL-12p40, IL-12p70, IL-13, IL-15, IL-17, interferon gamma-induced protein 10 (IP-10), monocyte chemoattractant protein 1 (MCP-1), monocyte chemoattractant protein 3 (MCP-3), macrophage inflammatory protein 1a (MIP-1a), macrophage inflammatory protein 1b (MIP-1b), regulated on activation, normal T cell expressed and secreted (RANTES), tumor necrosis factor alpha (TNF-a), tumor necrosis factor beta (TNF-b) and vascular endothelial growth factor A (VEGF-A) 25 ul of culture medium was assayed in duplicate as directed by the manufacturer and detected on a Luminex xMAP platform.

Achilles Tendon Healing Model—All procedures were approved by the University of Wisconsin Institutional Animal Care and Use Committee. All surgeries were performed using isofluorane, and all efforts were made to minimize suffering. Fifty-two skeletally mature male nude (Foxn1nu) mice (9-10 weeks old) were used as an animal model to study normal Achilles tendon healing after surgical transection. A surgically transected rather than torn tendon was used as an experimental model to create a uniform defect for healing. Mice were anesthetized via isofluorane and subjected to unilateral Achilles tendon transection. A skin incision was made, and the subcutaneous tissue was dissected to expose the underlying Achilles and superficial digital flexor (SDF) tendon of the right limb. The SDF was separated from the Achilles tendon and removed. The Achilles tendon was then completely transected at the mid-point (half way between the calcaneal insertion and the musculotendinous junction; determined using a scaled scalpel handle). Tendon ends were sutured together using 5-0 Vicryl suture. Two experiments were included in this study. In the first experiment, treatments (20 ul) were administered directly to the Achilles tendon and included 1) injury only (n=11), 2) $1\times10^{\wedge}6$ hMSC (n=11), 3) $1\times10^{\wedge}6$ CD14$^+$ macrophages (M0; n=11), and 4) EEMs isolated from $1\times10^{\wedge}6$ MSCs (n=11). Use of hMSCs as a treatment served as the gold standard for tendon treatment. The left Achilles tendon remained intact and served as the control. For the second experiment, injured Achilles tendons were treated with exosomes isolated from $1\times10^{\wedge}6$ BM-MSCs (n=8). Following transection and repair of Achilles tendon the joint was immobilized using a wire cerclage. A hole was drilled in the tuber calcaneus. Surgical steel suture was passed proximally, through the fibular-tibial fork, and distally through the hole in tuber calcaneus. The wire ends were twisted together and tightened, placing the hock in full plantar flexion. The skin was sutured closed after insertion of the cerclage and transection/repair of the Achilles. Tendons were collected at days 7 and 14 and used for mechanical testing and/or immunohistochemistry/histology. Tissue from animals treated with exosomes in the second experiment were only collected at day 14. Tendons used for immunohistochemistry (IHC) were carefully dissected and immediately embedded longitudinal/frontal, in optimal cutting temperature (O.C.T.) medium for flash freezing. Animals used for mechanical testing, were sacrificed and limbs were stored in toto at −70 C until used. Mechanical testing was not performed on day 7 because tendons were too structurally compromised for meaningful data with our testing method.

Immunohistochemistry (IHC)/Histology—In order to identify cellular and ECM changes within the healing tendon after treatment, IHC and histology were performed on day 7 and 14 Achilles tendons. Longitudinal cryosections were cut at a 5 µm thickness, mounted on Colorfrost Plus microscope slides and maintained at −70 C. IHC was performed on frozen sections. Cryosections were fixed in acetone, exposed to 3% hydrogen peroxide to eliminate endogenous peroxidase activity, blocked with Rodent Block M (Biocare Medical, Pacheco, Calif.) and incubated with rabbit or rat primary antibodies. Primary rat monoclonal antibodies specific to mouse F4/80, CD206, CD31 (all 1:100, BioRad, Hercules, Calif.) were used to detect total macrophages, M2 macrophages, and endothelial cells, respectively. Rabbit polyclonal antibodies were used for type I collagen (1:800, Abcam-Serotec, Raleigh, N.C.) and type III collagen (1:150, Abcam-Serotec, Raleigh, N.C.). Lastly, rabbit monoclonal CCR7 was used to identify M1 macrophages (1:1200, Abcam-Serotec, Raleigh, N.C.). After primary antibody incubation, samples were exposed to Rabbit or Rat HRP Polymer (Biocare Medical, Pacheco, Calif.). The bound antibody complex was visualized using diaminobenzidine (DAB). Stained sections were dehydrated, cleared, coverslipped and viewed using light microscopy. After IHC staining, micrographs were collected using a camera assisted microscope (Nikon Eclipse microscope, model E6000 with an Olympus camera, model DP79). Images of 3-6 sections were captured and counted per animal. Images captured for measurement of total macrophages, M1 and M2 macrophages, endothelial cells, type I collagen, and type III collagen were quantified via Image J (National Institutes of Health, NIH). Measurements were collected 1) within the granulation tissue and 2) within the entire section. Tendon cryosections were also H&E stained to observe general morphology of the healing tendon.

Fractal analysis—Fractal analysis is a useful quantitative method to evaluate collagen matrix organization and for measuring the rate of healing and scar formation. All H&E stained sections were cropped 4.5 in×4.5 inches to include the transected region. Tendons were prepared and tested as described in our previous publications. See Chamberlain et al. (Chamberlain C S, Crowley E M, Kobayashi H, Eliceiri K W, Vanderby R (2011) Quantification of collagen organization and extracellular matrix factors within the healing ligament. Microsc Microanal 17: 779-787.) and Frisch et al. (Frisch K E, Duenwald-Kuehl S E, Kobayashi H, Chamberlain C S, Lakes R S, and Vanderby R (2012) Quantification of collagen organization using fractal dimensions and Fourier transforms. Acta Histochemica 114(2):140-144) which are incorporated herein by reference.

Mechanical Testing—In order to test the functional mechanical properties of the healing tendon after macrophage treatment, day 14 tendons were mechanically tested. Achilles tendons were dissected and surrounding tissue excised with care to keep the calcaneal insertion site intact. Tendons remained hydrated using phosphate-buffered saline (PBS). Tendon length, width, and thickness were measured using digital calipers and the cross-sectional area (assumed to be an ellipse) was estimated. Tendons were tested in a custom-designed load frame which held and loaded tendons along the longitudinal axis of the tissue. The calcaneus was trimmed and press-fit into a custom bone grip. The soft tissue end was fixed to strips of Tyvek (McMaster-Carr, Elmhurst, Ill.) with adhesive (super glue gel; Ace Hardware Corporation, Oak Brook, Ill.) which were held between two plates of the soft-tissue grip. Dimension measurements for the tendons were recorded at pre-load. Mechanical testing was performed at room temperature. A low preload of 0.1N was applied in order to obtain a uniform zero point prior to preconditioning (20 cycles at 0.5 Hz) to 0.5%. Pull-to-failure testing was performed on tendons at a rate of 3.33 mm/sec. Force and displacement information from the test system were recorded at 10 Hz during testing. Failure force was recorded as the highest load prior to failure of the tendon and stress was calculated by dividing the failure force by the initial cross-sectional area of the tendon.

Statistical Analysis—For mice studies, a one-way analysis of variance (ANOVA) was used to examine treatment differences for the IHC and mechanical data. If the overall p-value for the F-test in ANOVA was significant, post-hoc comparisons were performed using the Fisher's LSD method. Experimental data are presented as the means±S.E.M. All p-values reported are two sided. Computations and figures were performed using KaleidaGraph, version 4.03 (Synergy Software, Inc., Reading, Pa.). For flow cytometry, multiple t-tests were performed to determine significance. For the multiplex ELISA one-way ANOVA with Dunnett's multiple comparisons tests were performed. These computations were performed and figures generated using GraphPad prism version 7.02. P values at <0.05 were used as the criterion for statistical significance.

Results

EV measurements—A preparation of extracellular vesicles (EVs) from the MSCs was characterized to determine mean particle size and concentration of EVs using the IZON qNano particle characterization system. Mean particle size was found to be 160 nm in size and the mode particle size was 111 nm. The particle concentration yield from the various MSC isolates was consistent, all producing on average about $1\times10^{11}$ particles/ml. Based upon particle size by IZON qNano particle analysis, the vast majority of the EV preparation constituted exosome-sized vesicles. MSCs derived from BM or tendon produced similar sized exosomes at similar yields.

TABLE 2

Exosome characterization by IZONqnano.

| MSC tissue type and isolate | Mean particle size (nm) | Mode particle size (nm) | Concentration (particle/ml) |
| --- | --- | --- | --- |
| BM MSC (15PH05 P6) | 169 | 110 | $8.2 \times 10^{10}$ |
| BM MSC (15PH06 P4) | 162 | 108 | $1.6 \times 10^{11}$ |
| BM MSC (3364 P5) | 169 | 107 | $1.6 \times 10^{11}$ |
| Tendon MSC (hamstring Hu-tendon cells P3) | 165 | 112 | $1.1 \times 10^{11}$ |
| Tendon MSC (Hu-tendon cells P3) | 165 | 121 | $2.0 \times 10^{11}$ |

EEM flow cytometry—To characterize the immune-phenotype of EEMs compared to control macrophages, we examined expression of several M2 surface markers expressed on CD14+ macrophages isolated from two biologic isolates. These markers include: CD163, a scavenger receptor known to play a role in resolving inflammation and binding of hemoglobin: haptoglobin complexes, CD206, a mannose receptor shown to be elevated in MSC-educated macrophages (MEMs) and PD-L1 an immune-inhibitory checkpoint molecule. As shown in FIGS. 1A-1B, elevated expression of CD163, CD206 and PD-L1 of both the MFI and % cells was seen in the BM-EEMs. PD-L1 expression was significantly higher in EEMs relative to control macrophages. The results indicate that the EVs from the MSCs can activate the macrophages to become more M2-like. In addition to the markers noted above, M2 markers (PD-L2) and several M1 markers (CD86 and HLA-DR) were examined by flow cytometry to compare the immune-phenotype of the BM-EEMs and tendon-EEMs to control macrophages. As shown in FIGS. 1D (MFI) and 1E (percent cells), BM-EEMs have elevated expression of CD163, CD206, PD-L1, PD-L2, and CD16. Expression of CD206, as measured by MFI and percent cells, PD-L1, as measured by MFI, and CD163, as measured by percent cells, was statistically significant in the BM-EEMs as compared to macrophage controls. The M1 markers CD86 and HLA-DR were not significantly elevated. However, the tendon-EEMs gave a very different marker profile compared to BM-EEMs. Expression of both the M1 and M2 markers in the tendon-EEMs were found to be similar to macrophage controls.

Secretion profile of EEMs by Multiplex ELISA—BM-EEMs showed significant increases in secretion of immunomodulatory and growth factor compared to control macrophages (Table 3). BM-EEMs showed significant increases in secretion of Eotaxin, G-CSF, FRACTALKINE, INFa2, GRO, IL-7, IL-8, TNF-a, and VEGF-A compared to controls. The tendon-EEMs showed significantly decreased expression of IL-13 compared to control and the tendon-EEMs and significant decreases in INFa2, Eotaxin, and TGF-α compared to BM-EEMs.

TABLE 3

Secretion of cytokines, chemokines, and growth factors from control macrophages, BM-EEMs, and tendon-EEMs.

| Analyte (pg/ml) | Control | BM-EEM | Tendon-EEM |
| --- | --- | --- | --- |
| EGF | 0.6 | 0.0 | 0.0 |
| FGF-2 | 17.6 | 21.4 | 15.9 |
| EOTAXIN | 3.4 | 5.6* | 2.8 ## |
| TGF-a | 2.7 | 3.3 | 1.0 # |
| G-CSF | 26.5 | 62.4* | 30.8 |
| FLT-3L | 8.7 | 9.4 | 7.5 |
| GM-CSF | 9.0 | 12.0 | 8.9 |
| FRACTALKINE | 20.1 | 30.2* | 22.2 |
| INFa2 | 15.3 | 21.8* | 15.7 # |
| IFNg | 5.8 | 7.6 | 6.2 |
| GRO | 307.1 | 1249.6* | 386.8 |
| IL-10 | 38.4 | 45.0 | 33.8 |
| MCP-3 | 190.7 | 288.2 | 121.9 |
| IL-12p40 | 8.5 | 9.5 | 6.7 |
| MDC | 4826.0 | 5229.0 | 5023.7 |
| IL-12p70 | 2.6 | 3.5 | 2.2 |
| IL-13 | 4.4 $$$ | 3.9 $$ | 2.5*** ## |
| PDGF-BB | 90.4 | 117.8 | 108.1 |
| IL-15 | 2.0 | 2.2 | 1.5 |
| sCD40L | 5.6 | 7.0 | 4.8 |
| IL-17 | 1.1 | 1.6 | 0.0 |
| IL-1ra | 820.3 | 671.0 | 635.0 |
| IL-1a | 0.0 | 0.36 | 0.0 |
| IL-9 | 0.5 | 0.4 | 0.0 |
| IL-1b | 1.6 | 2.1 | 0.0 |
| IL-2 | 1.8 | 2.1 | 1.7 |
| IL-4 | 17.4 | 32.8 | 18.7 |
| IL-5 | 0.0 | 0.0 | 0.0 |
| IL-6 | 0.0 | 35.6 | 1.1 |
| IL-7 | 4.5 | 8.6* | 3.8 |
| IL-8 | 159.9 | 2251.0* | 184.6 |
| IP-10 | 42.7 | 53.6 | 35.7 |
| MCP-1 | 8567.7 | 9087.7 | 9035.0 |
| MIP-1a | 18.8 | 36.9 | 12.4 |
| MIP-1b | 36.6 | 125.0 | 27.7 |
| RANTES | 14.3 | 33.2 | 15.7 |
| TNFa | 4.0 | 14.4* | 3.7 |
| TNFb | 0.0 | 0.0 | 0.0 |
| VEGF | 27.4 | 47.3* | 26.7 |

Significance between the groups were designated as the following
*= significant compared to control,
# = significant compared to BM-EEM,
$ = significant compared to tendon-EEMs.

Specifically, increased secretion of chemotactic/chemoattractant chemokines (EOTAXIN, FRACTALKINE, IL-8), wound healing chemokine, (GRO), vascular growth factor (VEGF-A), hematopoietic growth factors (G-CSF and IL-7) and immunomodulatory cytokines (INFa2, TNF-alpha) by the BM-EEMs may contribute to the promotion of tendon repair. The secretion profile of the tendon-EEMs was very different from the BM-EEMs and more similar to the macrophage controls. There were significant decreases in EOTAXIN, INFa2 and TGF-a in the tendon-EEMs not increases as seen in the BM-EEMs. Moreover, the tendon-EEMs also secreted significantly less IL-13, a cytokine known to mediate inflammation, compared to both controls and BM-EEMs.

Figure 2A:
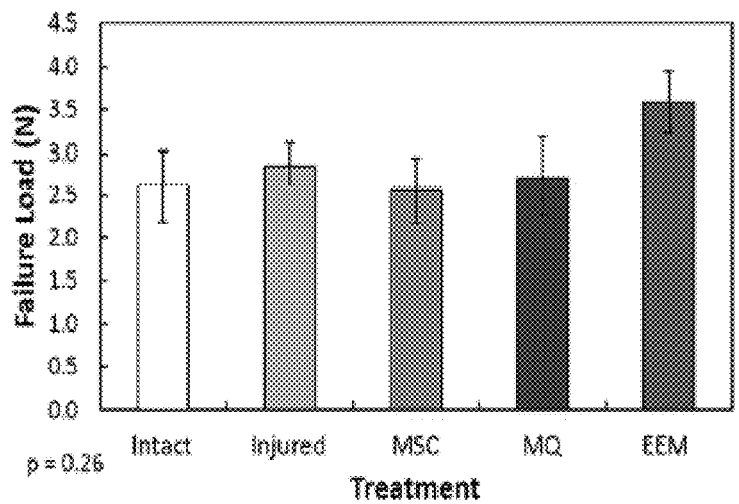
FIGS. 2A-2C demonstrate mechanical results of the healing Achilles tendon after macrophage treatment. Graphs show failure load (FIG. 2A), Young's modulus (FIG. 2B), and maximum stress (FIG. 2C) of the Achilles tendon 14 days post-injury after injury only, mesenchymal stem cell (MSC) treatment, macrophage treatment (M0), or EEM treatment. No significance was observed for failure load. In contrast, EEM treatment significantly improved Young's modulus (FIG. 2B) and maximum stress (FIG. 2C) compared to all other treatments. Results are expressed as mean±S.E.M.
Figure 2B:
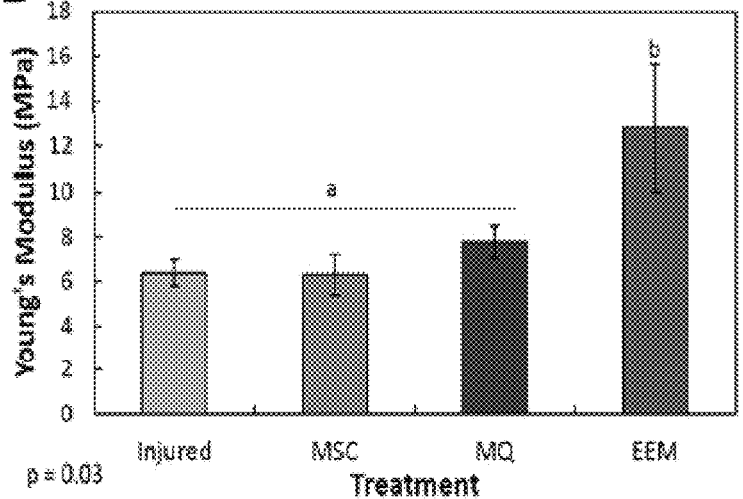
Figure 2C:
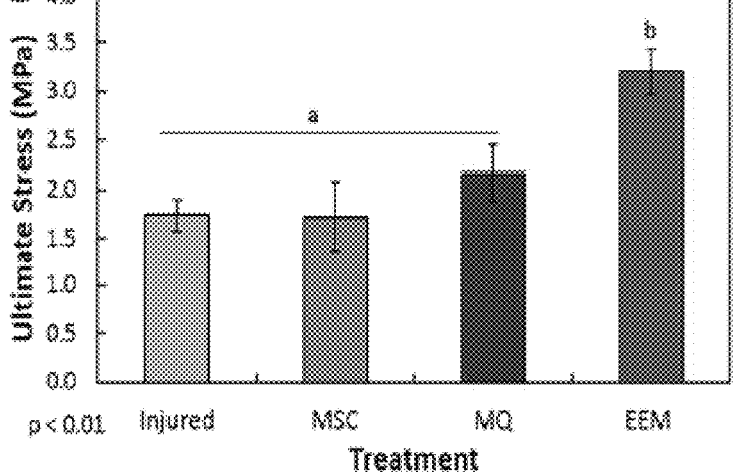

Mechanical testing—To determine if EEM treatment affected tendon function, the day 14 tendons (FIGS. 2A-2C) were mechanically tested. Tendon failure load, Young's modulus, and maximum stress were measured. No significant difference was found between any treatment groups for failure load (p=0.26; FIG. 2A). In contrast, compared to all other groups, EEM treatment significantly increased Young's modulus (p=0.03; FIG. 2B). Similarly, EEM treatment resulted in a significant increase in maximum stress (p=0.004; FIG. 2C). Altogether, these results indicate that EEM treatment improved the mechanical properties of the healing tendon even more substantially than the current gold standard treatment with MSC.

Figures 3A, 3S:
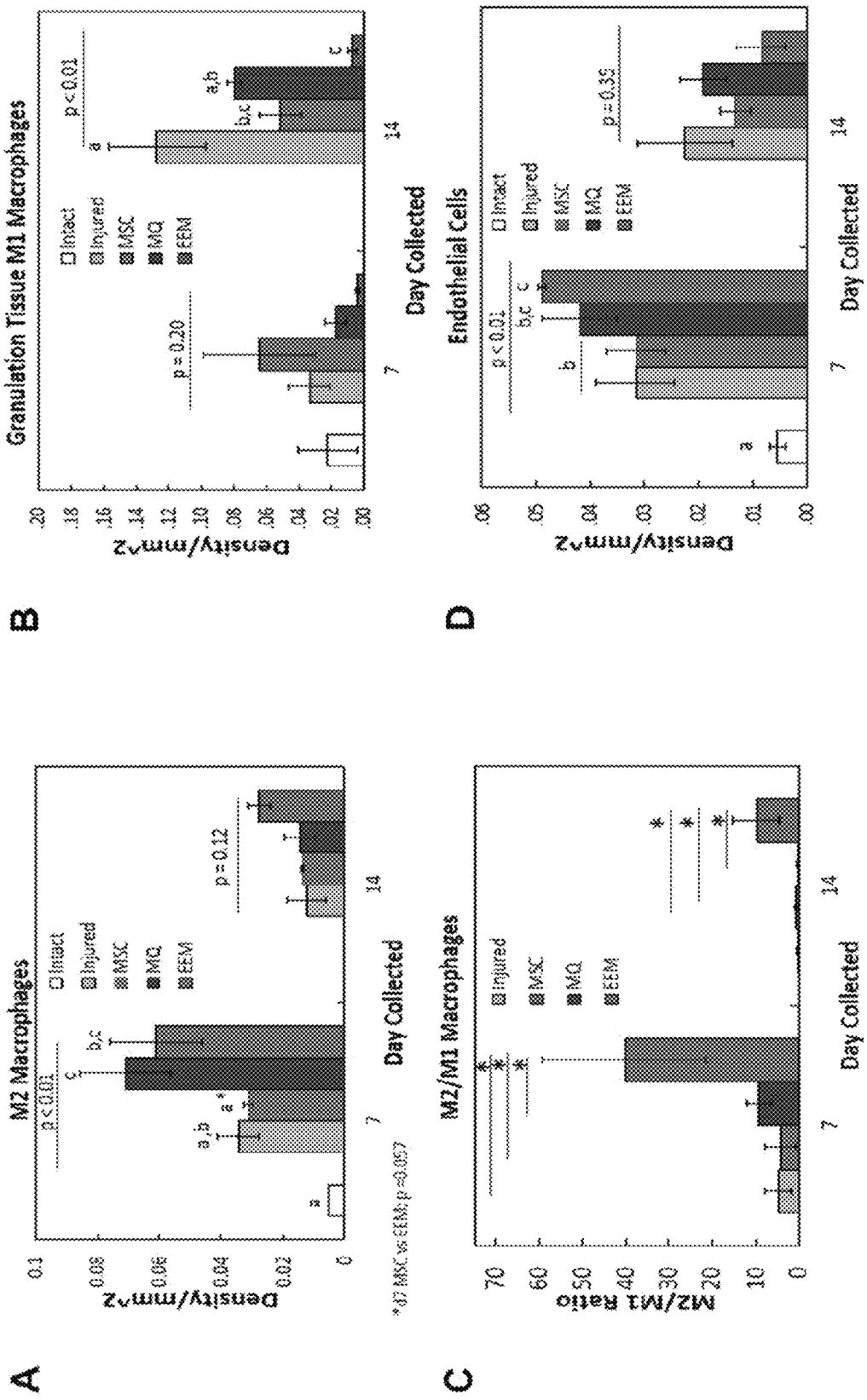
FIGS. 3A-3S demonstrate immunohistochemistry results of the day 7 and 14 healing tendon. Graphs of total endogenous M2 macrophages (FIG. 3A), endogenous M1 macrophages localized to the granulation tissue (FIG. 3B), endogenous M2/M1 macrophage ratio (FIG. 3C), endothelial cells (FIG. 3D) within the healing Achilles tendon after treatment with nothing (injured), MSCs, M0, or EEMs. Representative images of the endogenous M2 macrophages (FIGS. 3E-3I), endogenous M1 macrophages (FIGS. 3J-3N), endothelial cells (FIGS. 3O-3S) in the intact (FIGS. 3E, 3J, and 3O), day 7 injured (FIGS. 3F, and 3P), MSC (FIGS. 3G and 3Q), M0 (FIGS. 3H and 3R), EEM (FIGS. 3I and 3S), day 14 injured (FIG. 3K), MSC (FIG. 3L), MO (FIG. 3M), and EEM (FIG. 3N). "s" indicates sutures within the tissue. $*^{,a,b,c}$ indicates significance within a graph, bars without a common superscript letter differ significantly (results of Fisher's LSD post-hoc pairwise analysis, p<0.05). Values are expressed as mean cell numbers±S.E.M.
Figures 3A, 3S:
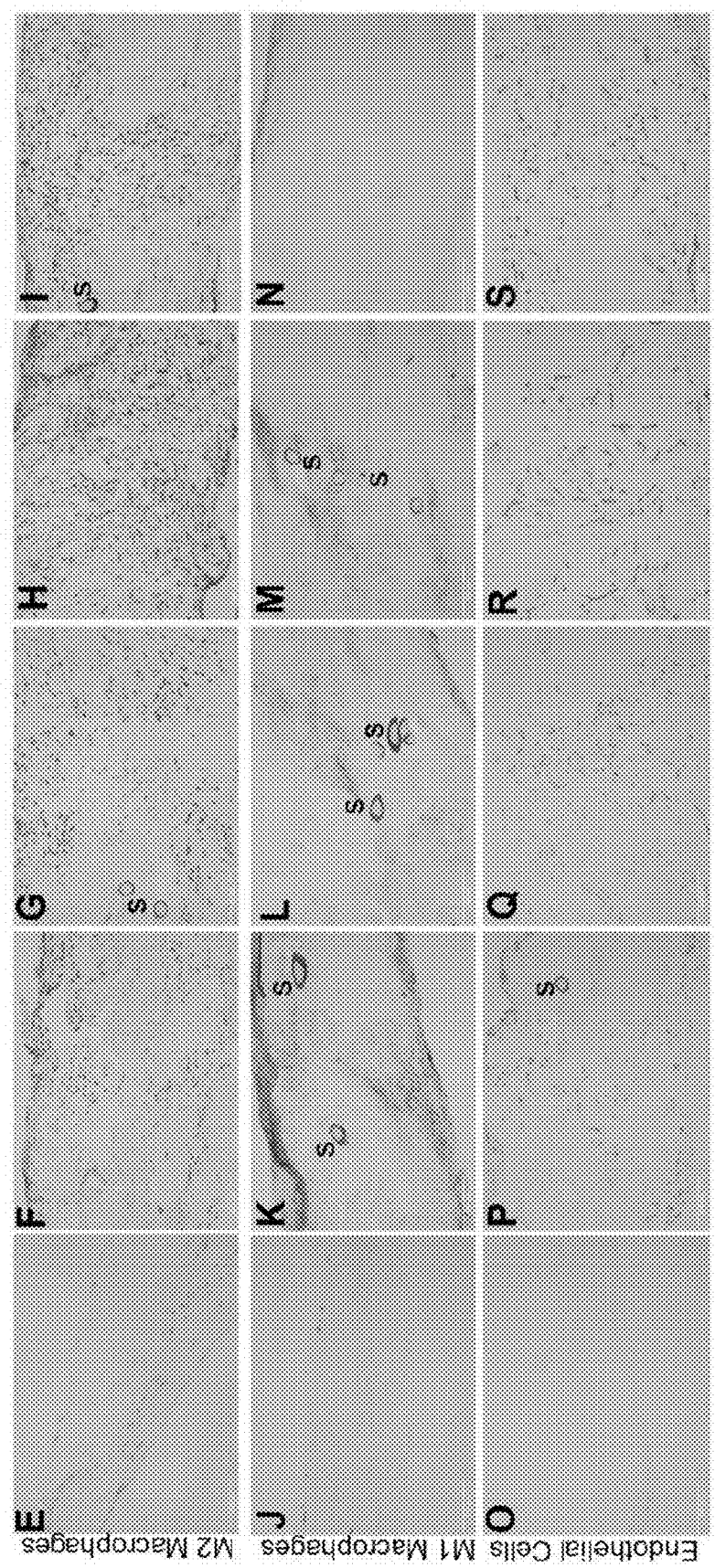
Figures 4A, 4B, 4C, 4D, 4E, 4F, 4G, 4H, 4I, 4J:
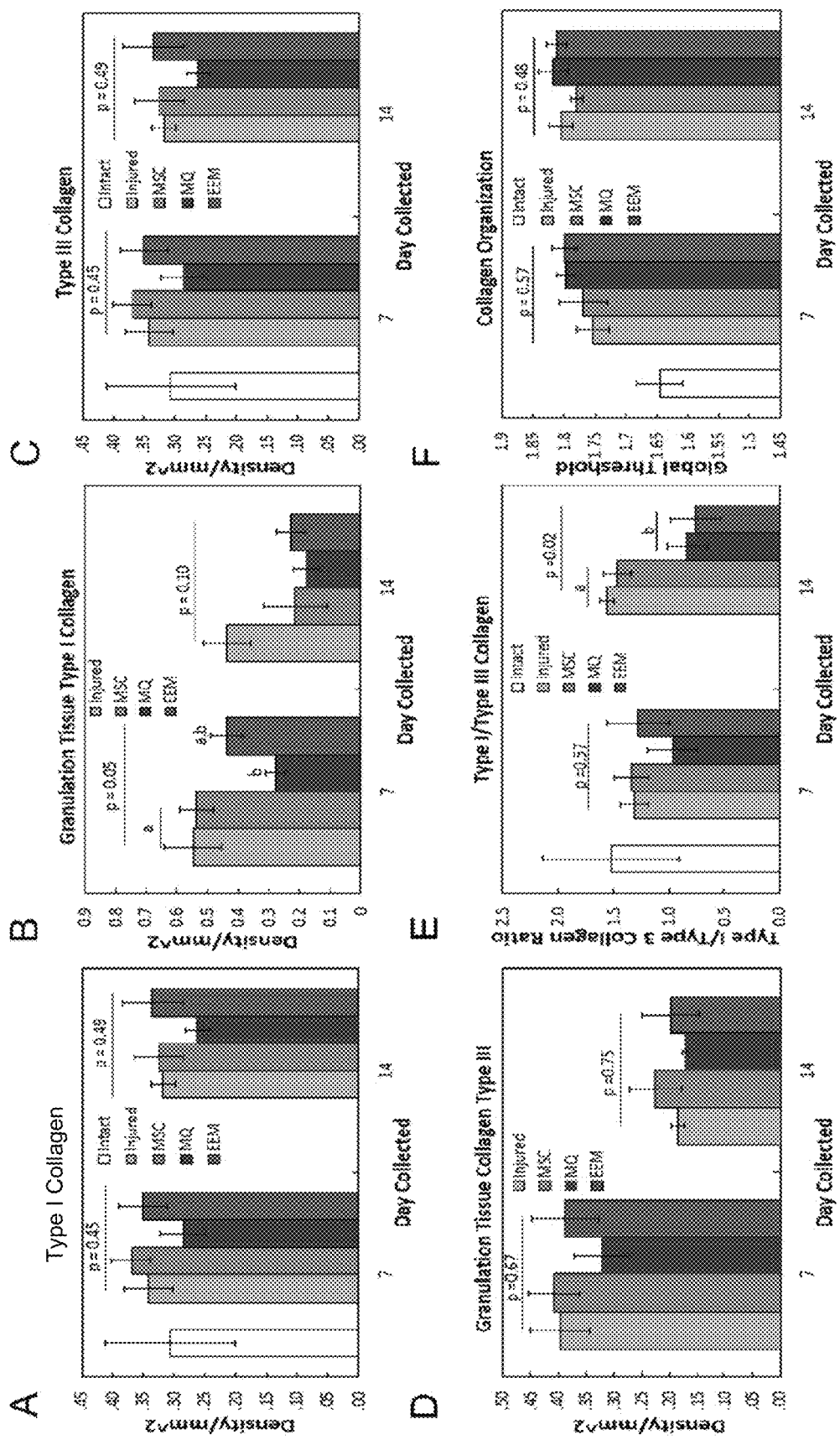
FIGS. 4A-4J demonstrate immunohistochemistry results of ECM factors by the day 7 and 14 healing tendon. Immunohistochemistry results showing the effects of MSCs, MQs, and EEMs on (FIG. 4A) type I collagen throughout entire tendon, (FIG. 4B) type I collagen within the granulation tissue, (FIG. 4C) type III collagen throughout entire tendon, (FIG. 4D) type III collagen within the granulation tissue, (FIG. 4E) Type I/Type III collagen ratio and (FIG. 4F) collagen organization.
Figures 4A, 4B, 4C, 4D, 4E, 4F, 4G, 4H, 4I, 4J:
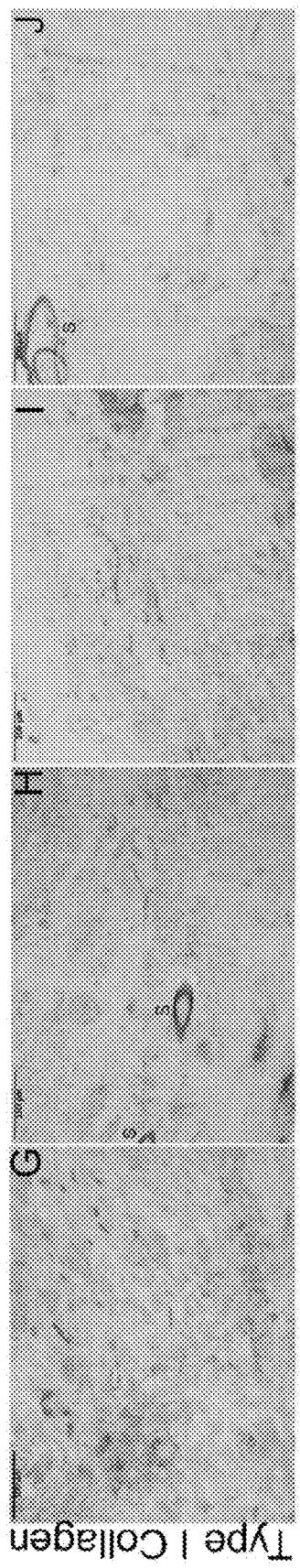
Figures 5A, 5B, 5C, 5D, 5E, 5F, 5G, 5H:
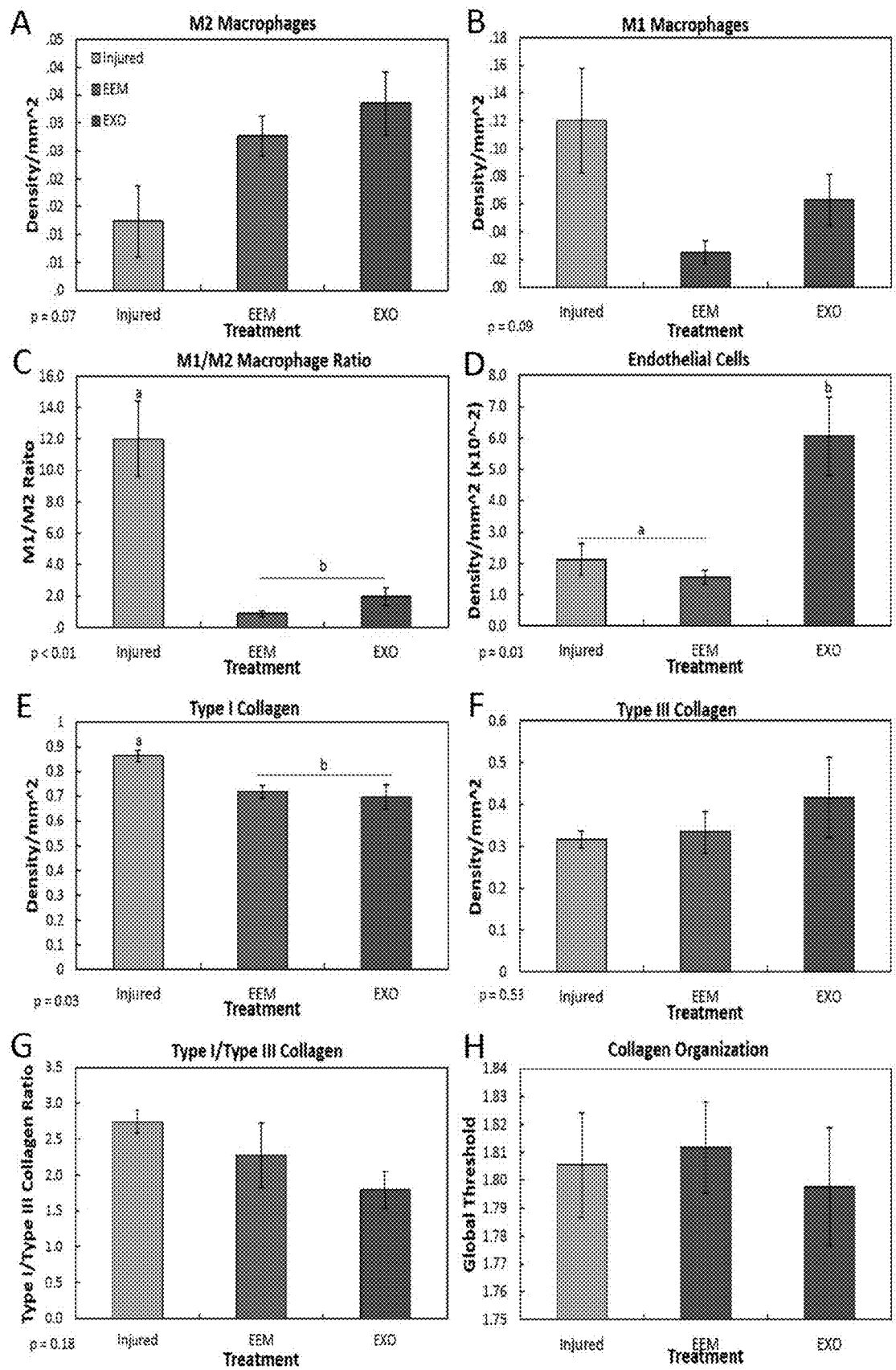
FIGS. 5A-5H demonstrate immunohistochemistry results of tendon healing. Graphs of total endogenous M2 macrophages (FIG. 5A), endogenous M1 macrophages (FIG. 5B), endogenous M1/M2 macrophage ratio (FIG. 5C), endothelial cells (FIG. 5D), type I collagen (FIG. 5E), type III collagen (FIG. 5F), type I/type III collagen ratio (FIG. 5G), and collagen organization (FIG. 5H) within the healing Achilles tendon after treatment with nothing (injured), EEMs, or exosomes alone (EXO).
Figures 6A, 6B, 6C, 6D:
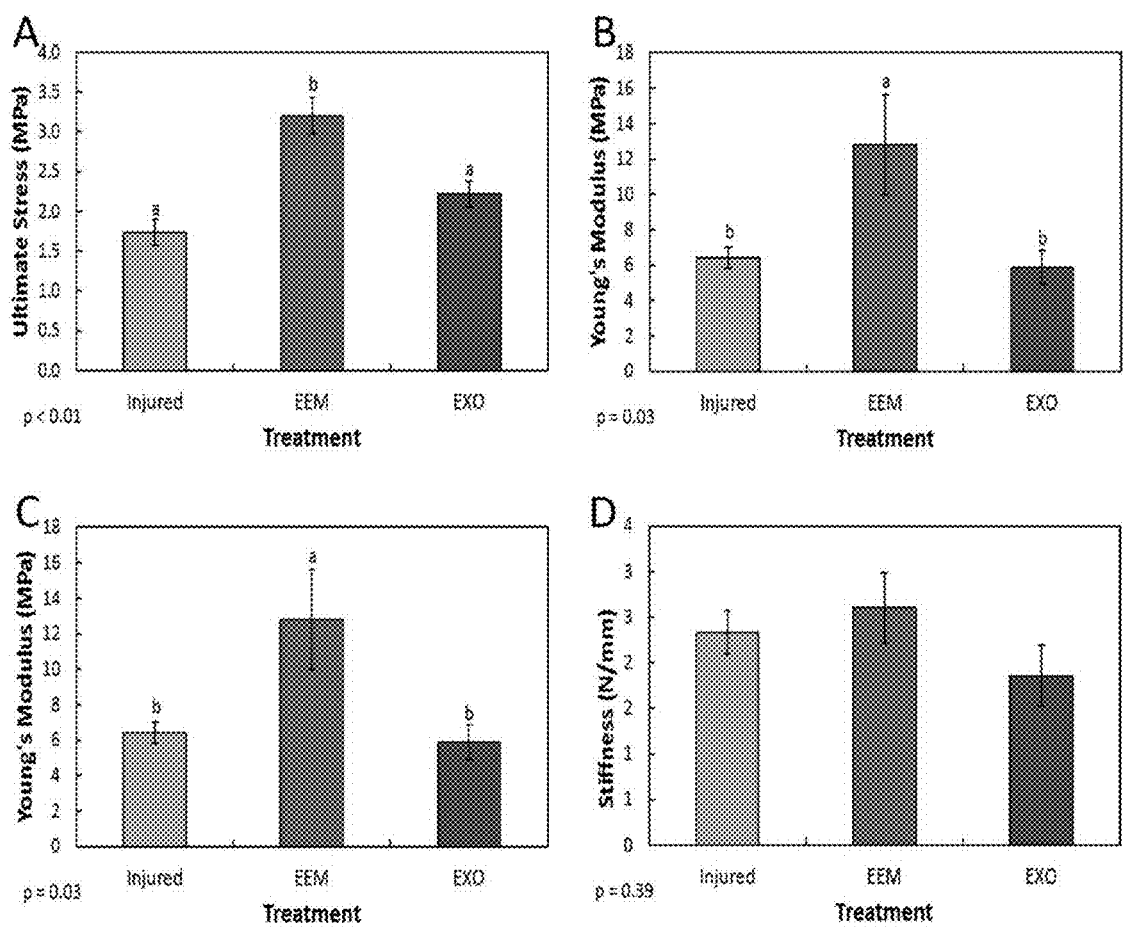
FIGS. 6A-6D demonstrate mechanical results of the healing Achilles tendon model. Histograms show ultimate stress (FIG. 6A), Young's modulus (FIG. 6B), Young's modulus (FIG. 6C), and stiffness (FIG. 6D) of the Achilles tendons after treatment with nothing (injured), EEMs, or exosomes alone (EXO).

IHC of cellular factors—IHC was performed to determine whether administration of exogenous EEMs affects endogenous cellular production of macrophages. The total number of macrophages was not significantly different between treatment groups at day 7 (p=0.97) or 14 (p=0.25). However, phenotypic analysis of the macrophages indicated that the number of day 7 endogenous M2 macrophages was significantly increased after both macrophage (p=0.004) or EEM treatment compared to tendon injury without treatment ("injury") or MSC treatment (FIGS. 3A, 3E-3I). Interestingly, M2 macrophages within the gold standard MSC treated group were similar to the injury only group. By day 14, the number of M2 macrophages were reduced compared to day 7. Compared to other treatments, EEMs significantly reduced the number of M1 macrophages within the granulation tissue day 14 (FIGS. 3B, 3J-3N). Additional examination of the macrophages indicated a decrease in the M1/M2 ratio at day 14 after EEM treatment (FIG. 3C). Lastly, EEM treatments also increased the number of day 7 endothelial cells (FIGS. 3D, 3O-3S), indicating earlier angiogenesis in the repair cascade with EEM treatment. No changes were noted by day 14, indicating that step in the healing process ended earlier with EEM treatment.

REFERENCES

1. Chiodo C P, Wilson M G (2006) Current concepts review: acute ruptures of the achilles tendon. Foot & Ankle International 27: 305-313.
2. de Jong J P, Nguyen J T, Sonnema A J, Nguyen E C, Amadio P C, et al. (2014) The incidence of acute traumatic tendon injuries in the hand and wrist: a 10-year population-based study. Clin Orthop Surg 6: 196-202.
3. Wynn T A (2004) Fibrotic disease and the T(H)1/T(H)2 paradigm. Nature Reviews Immunology 4: 583-594.
4. Xiao W, Hong H, Kawakami Y, Lowell C A, Kawakami T (2008) Regulation of myeloproliferation and M2 macrophage programming in mice by Lyn/Hck, SHIP, and Stat5. J Clin Invest 118: 924-934.
5. Godwin J W, Pinto A R, Rosenthal N A (2013) Macrophages are required for adult salamander limb regeneration. Proc Natl Acad Sci USA 110: 9415-9420.
6. Aktas E, Chamberlain C S, Saether E E, Duenwald-Kuehl S E, Kondratko-Mittnacht J, et al. (2016) Immune modulation with primed mesenchymal stem cells delivered via biodegradable scaffold to repair an Achilles tendon segmental defect. J Orthop Res.
7. Saether E E, Chamberlain C S, Aktas E, Leiferman E M, Brickson S L, et al. (2016) Primed Mesenchymal Stem Cells Alter and Improve Rat Medial Collateral Ligament Healing. Stem Cell Rev 12: 42-53.
8. Chamberlain C S, Saether E E, Aktas E, Vanderby R (2017) Mesenchymal Stem Cell Therapy on Tendon/Ligament Healing. J Cytokine Biol 2.
9. Shen H, Kormpakis I, Havlioglu N, Linderman S W, Sakiyama-Elbert S E, et al. (2016) The effect of mesenchymal stromal cell sheets on the inflammatory stage of flexor tendon healing. Stem Cell Research & Therapy 7: 144.
10. Sindrilaru A, Peters T, Wieschalka S, Baican C, Baican A, et al. (2011) An unrestrained proinflammatory M1 macrophage population induced by iron impairs wound healing in humans and mice. J Clin Invest 121: 985-997.
11. Benoit M, Desnues B, Mege J L (2008) Macrophage polarization in bacterial infections. J Immunol 181: 3733-3739.
12. Weisberg S P, McCann D, Desai M, Rosenbaum M, Leibel R L, et al. (2003) Obesity is associated with macrophage accumulation in adipose tissue. Journal of Clinical Investigation 112: 1796-1808.
13. Kim J, Hematti P (2009) Mesenchymal stem cell-educated macrophages: a novel type of alternatively activated macrophages. Exp Hematol 37: 1445-1453.
14. Bouchlaka M N, Moffitt A B, Kim J, Kink J A, Bloom D D, et al. (2017) Human Mesenchymal Stem Cell-Educated Macrophages Are a Distinct High IL-6-Producing Subset that Confer Protection in Graft-versus-Host-Disease and Radiation Injury Models. Biol Blood Marrow Transplant 23: 897-905.
15. Frisch K E, Duenwald-Kuehl S E, Kobayashi H, Chamberlain C S, Lakes R S, et al. (2012) Quantification of collagen organization using fractal dimensions and Fourier transforms. Acta Histochem 114: 140-144.
16. Chamberlain C S, Crowley E M, Kobayashi H, Eliceiri K W, Vanderby R (2011) Quantification of collagen organization and extracellular matrix factors within the healing ligament. Microsc Microanal 17: 779-787.
17. Moestrup S K, Moller H J (2004) CD163: a regulated hemoglobin scavenger receptor with a role in the anti-inflammatory response. Ann Med 36: 347-354.
18. Deng W, Chen W, Zhang Z, Huang S, Kong W, et al. (2015) Mesenchymal stem cells promote CD206 expression and phagocytic activity of macrophages through IL-6 in systemic lupus erythematosus. Clin Immunol 161: 209-216.
19. Dominici M et al. Minimal criteria for defining multipotent mesenchymal stromal cells. The International Society for Cellular Therapy position statement Cytotherapy 8(4):315-317 (2006)

Example 2

In a proof of concept in vivo study, BM-EEMs were used in a rat medial collateral ligament (MCL) injury model. We observed a significant increase in strength by the healing ligament after EEM treatment when compared to control animals.

Animal Preparation—All procedures were approved by the University of Wisconsin Institutional Animal Use and Care Committee. Four 5 week old male Foxn1$^{-/-}$ (nude) rats were used as an animal model for ligament healing. Rats were anesthetized via isofluorane. Each rat was subjected to bilateral medial collateral ligament (MCL) transections using sterile techniques. A surgically transected, rather than torn ligament is used as an experimental model to create a uniform defect for healing. A small, 1 cm skin incision was made over the medial aspect at both the left and right stifles. Then the subcutaneous tissue was dissected to expose the sartorius muscle and underlying MCL. The mid-point of the MCL was completely transected, leaving the knee capsule intact. The muscular layer was partially sutured with 5-0 Vicryl, creating a pouch. Treatment was administered within the pouch before muscle was closed with suture. Treatment included $1.5\times10^6$ EEMs per ipsilateral side. The injured contralateral MCL received Hanks balanced saline solution (HBSS) and served as the control. Subcutaneous and subdermal tissue layers were each closed with 5-0 Vicryl suture. All animals were allowed unrestricted cage movement immediately after surgery.

Mechanical Testing—The day 14 healing ligaments were tested to determine the influence of EEM treatment on mechanical performance. After sacrifice the MCL was removed with both femoral and tibial insertion sites intact and the surrounding tissue was carefully excised with care taken to avoid damaging the insertion sites. During preparation, the femur-MCL-tibia (FMT) complex was kept hydrated using phosphate-buffered saline. The width and thickness of the ligament was measured optically and the cross-sectional area for the ligament was estimated assuming an elliptical cross section. The FMT complex was mounted in a custom made testing bath and mechanical testing machine. A pre-load of 0.1 N was applied to the ligament and the MCL was preconditioned (cyclically loaded to 1% strain for 10 cycles). Dimension measurements for the ligament were recorded at the pre-load. The ligament was then pulled to failure at a rate of 10% strain per second. Failure force was recorded as the highest load prior to failure of the ligament and failure stress was calculated by dividing the failure force by the initial cross-sectional area of the ligament. Failure strain was calculated by subtracting the initial ligament length from the ligament length at failure divided by the initial length of the ligament.

Figures 7A, 7B, 7C, 7D:
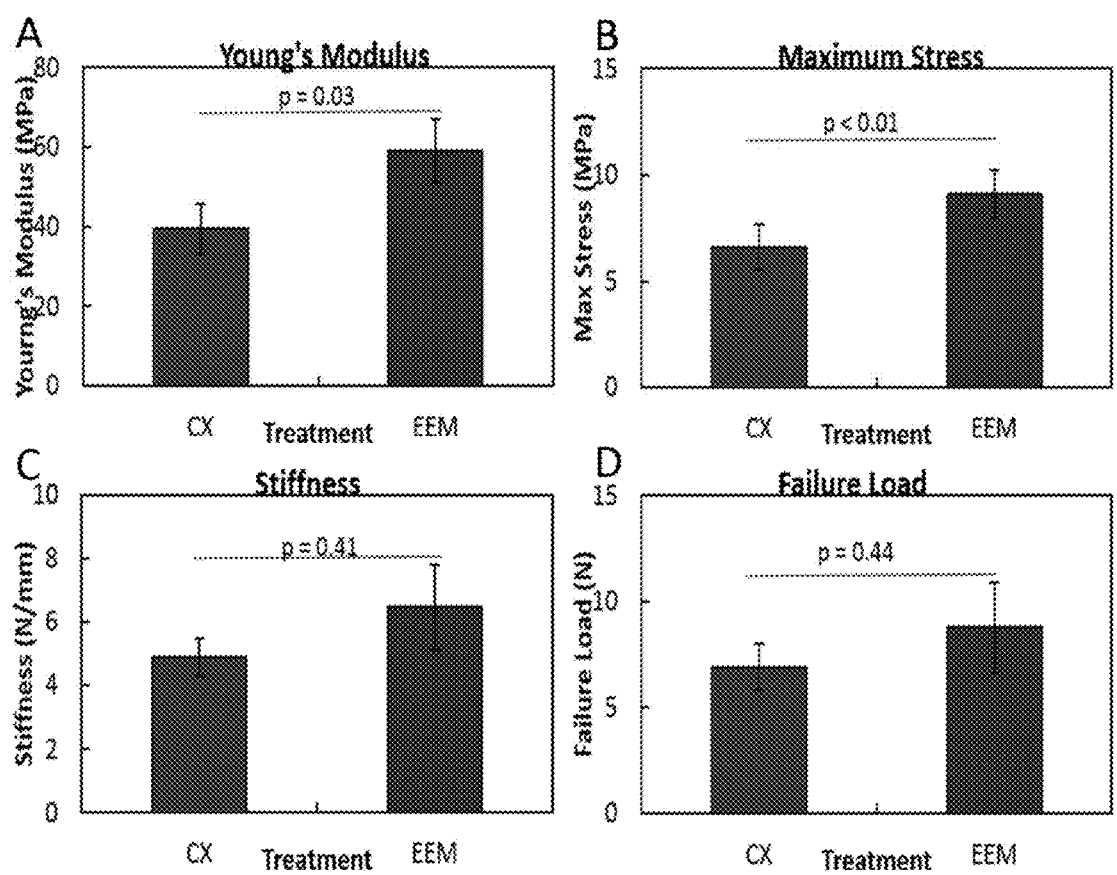
FIGS. 7A-7D demonstrate mechanical results of the healing medial collateral ligament (MCL). Histograms show Young's modulus (FIG. 7A), maximum stress (FIG. 7B), stiffness (FIG. 7C), and failure load (FIG. 7D) of the MCL after treatment with nothing (CX) or EEMs.

Results—Tendon failure load, ultimate stress, stiffness, and Young's modulus, were measured. Due to a technical error during mechanical testing, one animal was removed from the study. Compared to the injured controls, EEM treatment significantly increased Young's modulus (p=0.03; FIG. 7A). Similarly, EEM treatment resulted in a significant increase in ultimate stress (p<0.01; FIG. 7B). Although the mean value of the EEM treatment was the highest, no significant difference was found between any treatment groups for stiffness (p=0.41; FIG. 7C), and failure load (p=0.44; FIG. 7D). Altogether, using a rat MCL model, these results support that EEM treatment substantially improves the mechanical properties of the healing tendon.

We claim:

1. A method of treating an orthopedic injury to a ligament or a tendon in a subject in need thereof, the method comprising the step of:
   administering directly to the injured ligament or tendon of the subject a population of cells comprising bone marrow exosome educated macrophages (BM-EEM),
   wherein the BM-EEM comprise isolated peripheral CD14+ macrophages cultured with bone marrow mesenchymal stem cell-derived exosomes, and
   wherein administration of the cells to the subject improves mechanical properties of the injured ligament or tendon.

2. The method of claim 1, wherein the BM-EEM in the population are CD206 high, PD-L 1 high, PD-L2 high, TGF-high, TNF-a low, IL-6 high, and Serpine-1 high.

3. The method of claim 1, wherein the population of cells is administered by injection.

4. The method of claim 3, wherein the population of cells is administered by injection with a pharmaceutically acceptable carrier.

5. The method of claim 1, wherein the population of cells is administered surgically.

6. The method of claim 1, wherein the orthopedic injury to a ligament or a tendon is selected from the group consisting of a partial tendon tear, a complete tendon tear, a partial tendon laceration, a compete tendon laceration, a partial tendon avulsion, a complete tendon avulsion, a partial ligament tear, a complete ligament tear, a partial ligament laceration, a compete ligament laceration, tendinopathy, tendinosis, tendinitis, and joint capsule tears.

7. The method of claim 1, wherein the orthopedic injury to a ligament or a tendon is selected from the group consisting of plantar fasciitis, tennis elbow, bicep tendinitis, and carpal tunnel syndrome.

8. The method of claim 1, wherein the population of cells is administered at a dose between about $1\times10^4$ cells/kilogram and about $10\times10^9$ cells/kilogram of body weight of the subject.

9. A method of improving the mechanical properties of an injured ligament or tendon in a subject in need thereof, the method comprising the step of:
   administering directly to the injured ligament or tendon of the subject a population of cells comprising bone marrow exosome educated macrophages (BM-EEM),
   wherein the BM-EEM comprise isolated peripheral CD14+ macrophages cultured with bone marrow mesenchymal stem cell-derived exosomes; and
   increasing at least one of Young's modulus and maximum stress of the injured ligament or tendon.

10. The method of claim 1, wherein improvement in mechanical properties of the injured ligament or tendon is measurable by increases in at least one of Young's modulus and maximum stress of the injured ligament or tendon.

* * * * *

UNITED STATES PATENT AND TRADEMARK OFFICE
CERTIFICATE OF CORRECTION

| | |
|---|---|
| PATENT NO. | : 11,738,046 B2 |
| APPLICATION NO. | : 16/179298 |
| DATED | : August 29, 2023 |
| INVENTOR(S) | : Peiman Hematti et al. |

It is certified that error appears in the above-identified patent and that said Letters Patent is hereby corrected as shown below:

In the Claims

Claim 6, Column 24, Line 26, please replace "partial tendon laceration, a compete tendon laceration, a" with --partial tendon laceration, a complete tendon laceration, a--

Claim 6, Column 24, Line 29, please replace "laceration, a compete ligament laceration, tendinopathy," with --laceration, a complete ligament laceration, tendinopathy,--

Signed and Sealed this
Fourteenth Day of November, 2023

Katherine Kelly Vidal
*Director of the United States Patent and Trademark Office*